US012571795B2

(12) United States Patent  
Thiele et al.

(10) Patent No.: US 12,571,795 B2  
(45) Date of Patent: Mar. 10, 2026

(54) ANTI-MAA IMMUNOGLOBULIN ISOTYPES IN INFLAMMATORY BOWEL DISEASE: NOVEL DIAGNOSTIC IMPLICATIONS FOR ULCERATIVE COLITIS

(71) Applicant: Board of Regents of the University of Nebraska, Lincoln, NE (US)

(72) Inventors: Geoffrey M. Thiele, Omaha, NE (US); Amar Singh, Elkhorn, NE (US); Michael J. Duryee, Omaha, NE (US); Rizwan Ahmad, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 821 days.

(21) Appl. No.: 17/793,013

(22) PCT Filed: Jan. 15, 2021

(86) PCT No.: PCT/US2021/013646

§ 371 (c)(1),  
(2) Date: Jul. 14, 2022

(87) PCT Pub. No.: WO2021/146562

PCT Pub. Date: Jul. 22, 2021

(65) Prior Publication Data

US 2023/0075784 A1 Mar. 9, 2023

Related U.S. Application Data

(60) Provisional application No. 63/081,138, filed on Sep. 21, 2020, provisional application No. 62/961,372, filed on Jan. 15, 2020.

(51) Int. Cl.  
*G01N 33/543* (2006.01)  
*G01N 33/564* (2006.01)

(52) U.S. Cl.  
CPC ....... *G01N 33/564* (2013.01); *G01N 2440/10* (2013.01); *G01N 2800/065* (2013.01)

(58) Field of Classification Search  
None  
See application file for complete search history.

(56) References Cited

U.S. PATENT DOCUMENTS

| | | | |
|---|---|---|---|
| 10,591,468 B2 * | 3/2020 | Thiele .................. | G01N 33/564 |
| 2004/0241823 A1 | 12/2004 | Dieckmann et al. | |
| 2005/0136495 A1 | 6/2005 | Boone et al. | |
| 2009/0191208 A1 | 7/2009 | Salzman et al. | |
| 2012/0295264 A1 | 11/2012 | Kanaoka et al. | |
| 2021/0278417 A1 * | 9/2021 | M'Koma ............... | A61K 45/06 |

FOREIGN PATENT DOCUMENTS

| | | |
|---|---|---|
| WO | WO-2012125582 A1 | 9/2012 |
| WO | WO-2012170470 A1 | 12/2012 |
| WO | WO-2018220224 A1 | 12/2018 |
| WO | WO-2020056037 A1 | 3/2020 |
| WO | WO-2021146562 A1 | 7/2021 |

OTHER PUBLICATIONS

Thiele et al., Malondialdehyde-acetaldehyde adducts (MAA) and anti-MAA antibody in rheumatoid arthritis, Arthritis Rheumatol, Mar. 2015; 67(3): pp. 1-21. (Year: 2015).*  
Ahmad et al Anti-MAA Immunoglobulin Isotypes in Inflammatory Bowel Disease—Novel Diagnostic Implications for Ulcerative Colitis, Gatroenterology, vol. 156, No. 6, Suppl. 1, pp. S657-S658, May 2019). (Year: 2019).*  
Ahluwalia, B., et al., "Immunopathogenesis of Inflammatory Bowel Disease and Mechanisms of Biological Therapies," Scandinavian Journal of Gastroenterology, 2018, vol. 53(4), pp. 379-389.  
Ahmad, R., et al., "Malondialdehyde and Protein Carbonyl as Biomarkers for Oxidative Stress and Disease Progression in Patients With Chronic Myeloid Leukemia, " In vivo, 2008, vol. 22(4), pp. 525-528.  
Alzoghaibi, M., et al., "Lipid Peroxides in Patients With Inflammatory Bowel Disease," Saudi Journal of Gastroenterology, 2007, vol. 13(4), pp. 187-190.  
Anderson, D., et al., "Unique Antibody Responses to Malondialdehyde-acetaldehyde (Maa)-protein Adducts Predict Coronary Artery Disease," pLoS One, 2014, vol. 9(9), pp. 1-10.  
Bouzid, D., et al., "Oxidative Stress Markers in Intestinal Mucosa of Tunisian Inflammatory Bowel Disease Patients," Saudi Journal of Gastroenterology, 2013, vol. 19(3), pp. 131-135.  
Hedrick, T., et al., "Colonic Crohn Disease," Clinics in Colon and Rectal Surgery, 2013, vol. 26(2), pp. 84-89.  
Hendrickson, B., et al., "Clinical Aspects and Pathophysiology of Inflammatory Bowel Disease," Clinical Microbiology Reviews, 2002, vol. 15(1), pp. 79-94.  
Hill, G., et al., "Association of Malondialdehyde-acetaldehyde (Maa) Adducted Proteins With Atherosclerotic-induced Vascular Inflammatory Injury," Atherosclerosis, 1998, vol. 141(1), pp. 107-116.  
International Preliminary Report on Patentability dated Jul. 28, 2022 in PCT Application No. PCT/US2021/013646.  
International Search Report and Written Opinion dated Apr. 8, 2021 in PCT Application No. PCT/US2021/013646.  
Mikuls, T., et al., "Enrichment of Malondialdehyde-acetaldehyde Antibody in the Rheumatoid Arthritis Joint," Rheumatology, 2017, vol. 56(10), pp. 1794-1803.  
Pedersen, J., et al., Inflammatory pathways of importance for management of inflammatory bowel disease, World Journal of Gastroenterology, 2014, vol. 20(1), pp. 64-77.

(Continued)

*Primary Examiner* — Gary Counts  
(74) *Attorney, Agent, or Firm* — Weaver Austin Villeneuve & Sampson LLP

(57) ABSTRACT

In various embodiments methods of distinguishing Crohn's disease from ulcerative colitis are provided. In certain embodiments the methods comprise determining, or causing to be determined, the level of IgG antibodies that bind a malondialdehyde-acetaldehyde adduct (MAA adduct) in a biological sample from a mammal, where an elevated level of said antibodies as compared to the average level found in a mammal with Crohn's disease is an indicator that the mammal has ulcerative colitis rather than Crohn's disease.

17 Claims, 23 Drawing Sheets

(56)                    References Cited

OTHER PUBLICATIONS

Piechota-Polanczyk, A., et al., "Review Article: the Role of Oxidative Stress in Pathogenesis and Treatment of Inflammatory Bowel Diseases," Naunyn-schmiedeberg's Archives of Pharmacology, 2014, vol. 387(7), pp. 605-620.

Sapkota, M., et al., "Malondialdehyde-Acetaldehyde (MAA) Protein Adducts Are Found Exclusively in the Lungs of Smokers with Alcohol Use Disorders and Are Associated with Systemic Anti-MAA Antibodies," Alcoholism, clinical and experimental research, 2017, vol. 41(12), pp. 2093-2099.

Tuma, D., et al., "Acetaldehyde and Malondialdehyde React Together to Generate Distinct Protein Adducts in the Liver During Long-term Ethanol Administration," Hepatology, 1996, vol. 23(4), pp. 872-880.

Willis, M., et al., "Adduction of Soluble Proteins With Malondialdehyde-acetaldehyde (MAA) Induces Antibody Production and Enhances T-cell Proliferation," Alcoholism, clinical and experimental research, 2002, vol. 26(1), pp. 94-106.

Willis, M., et al., "T Cell Proliferative Responses to Malondialdehyde-acetaldehyde Haptenated Protein Are Scavenger Receptor Mediated," International immunopharmacology, 2003, vol. 3(10-11), pp. 1381-1399.

Torzewski M., et al., "Animal Models of C-Reactive Protein," Hindawl Publishing Corporation, Mediators of Inflammation, 2014, vol. 2014 , Articles 683598, pp. 1-7.

Vekens V D., et al., "Human and Equine Cardiovascular Endocrinology Beware to Compare," Cardiovascular Endocrinology, 2013, vol. 2 (4), pp. 67-76.

* cited by examiner

A

B

C
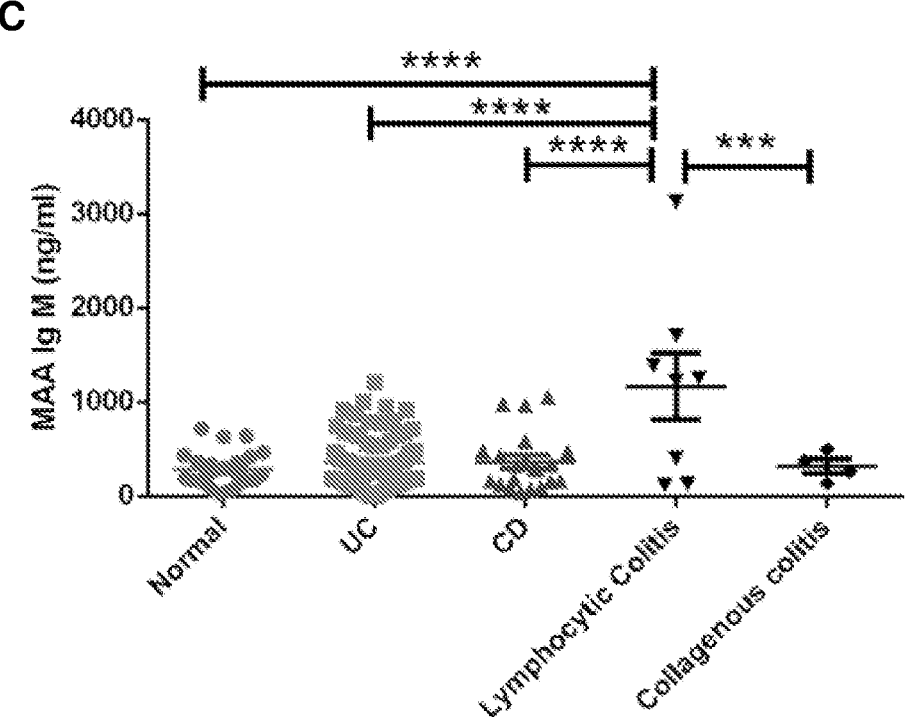
Fig. 1, cont'd.

A  Anti-MAA          Merge (Anti-MAA+DIC)

UC

CD

≫ Epithelial Cells
▓ Immune Cells

B

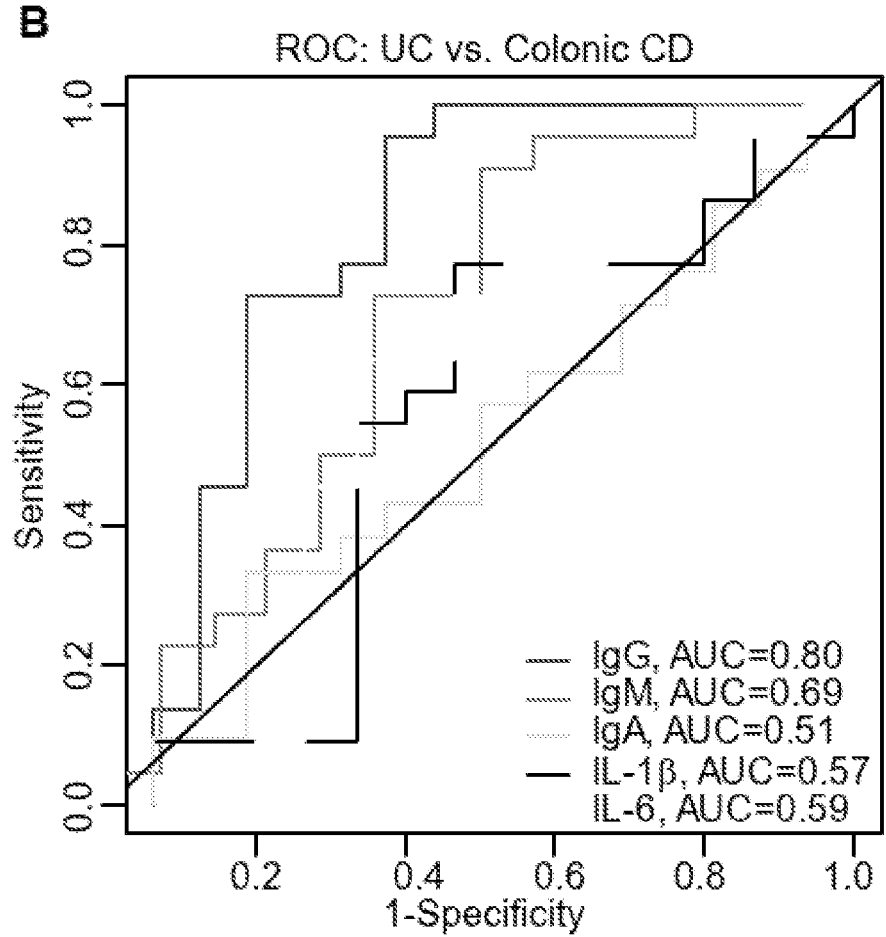
Fig. 5, cont'd.

C
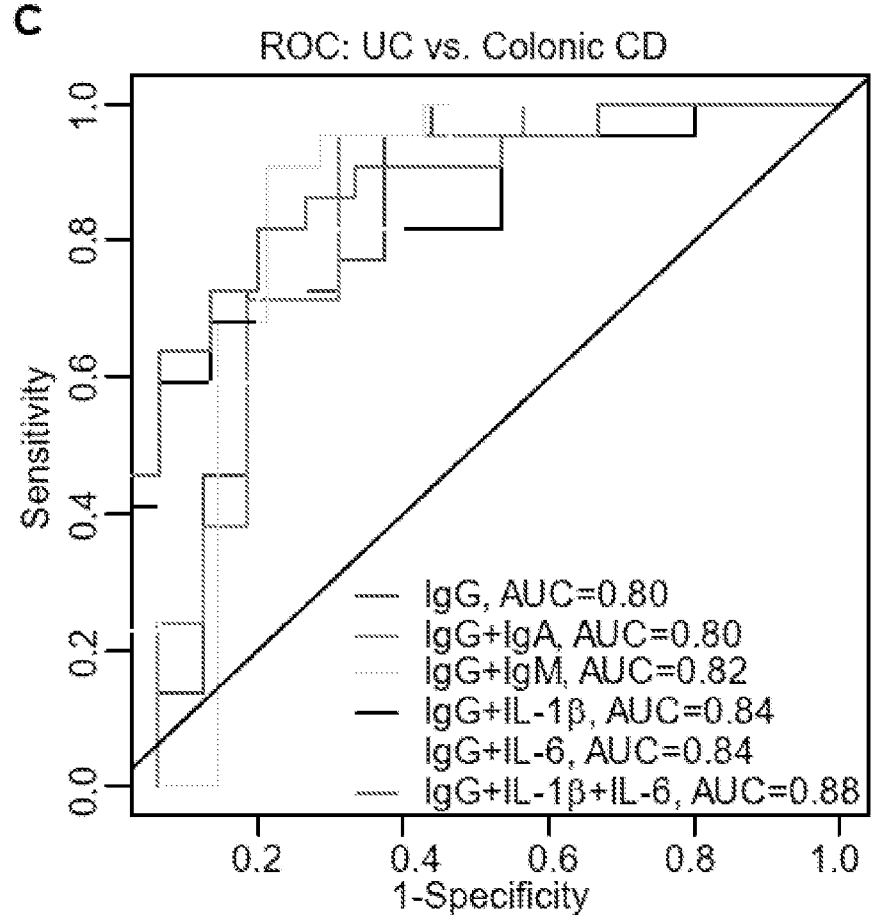
Fig. 5, cont'd.

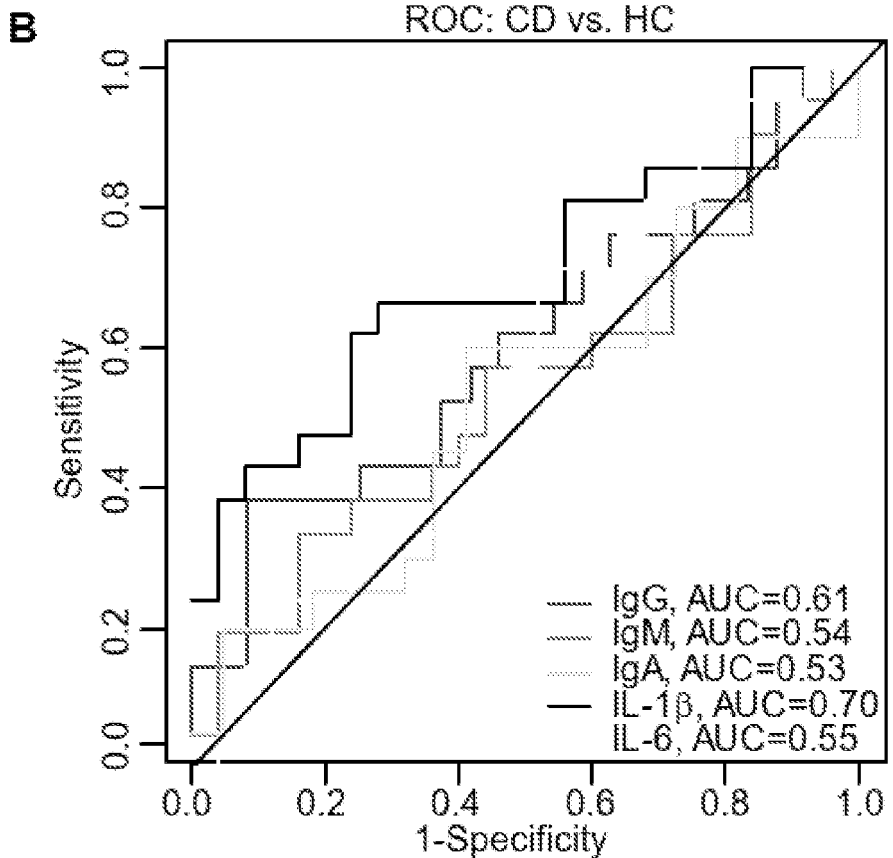
Fig. 6, cont'd.

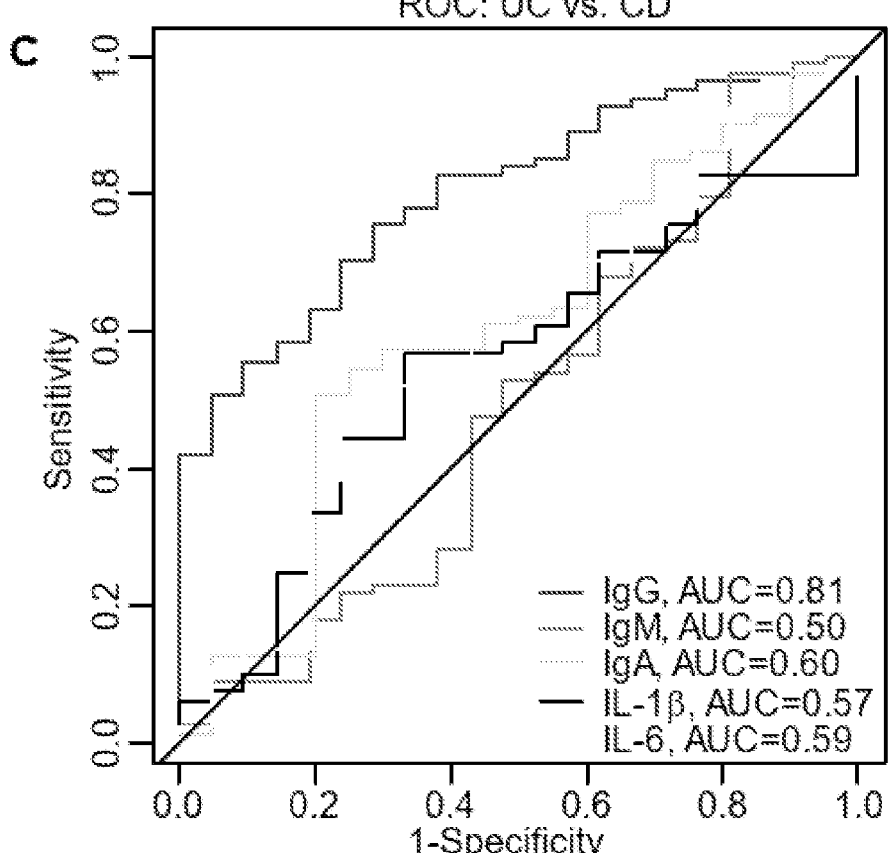
Fig. 6, cont'd.

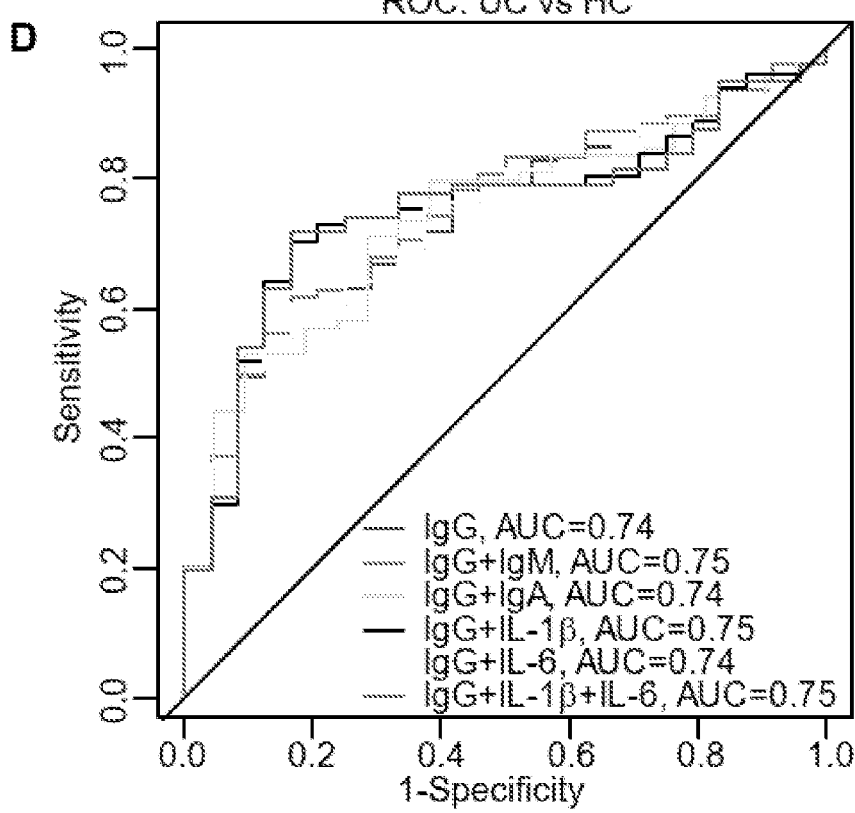
Fig. 6, cont'd.

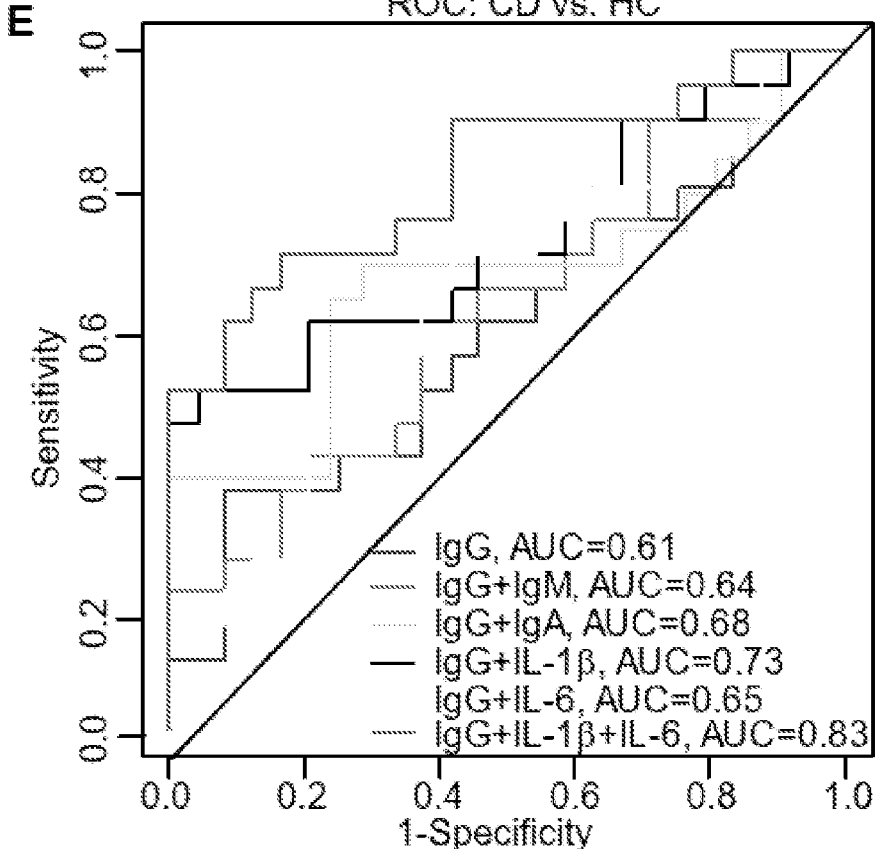
Fig. 6, cont'd.

F
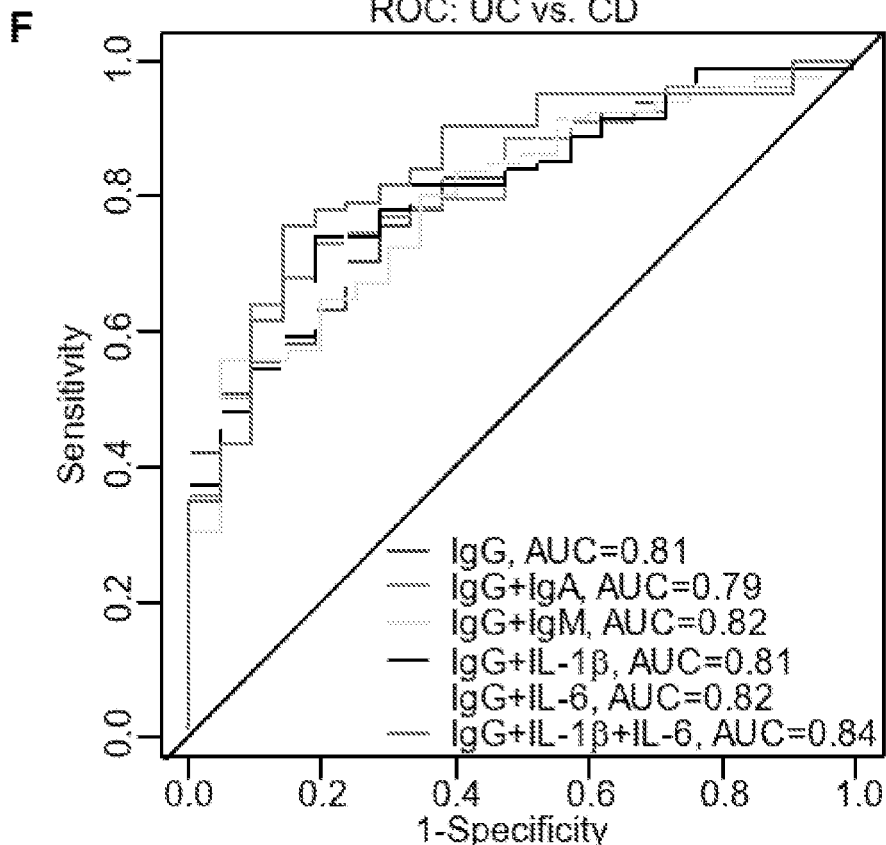
Fig. 6, cont'd.

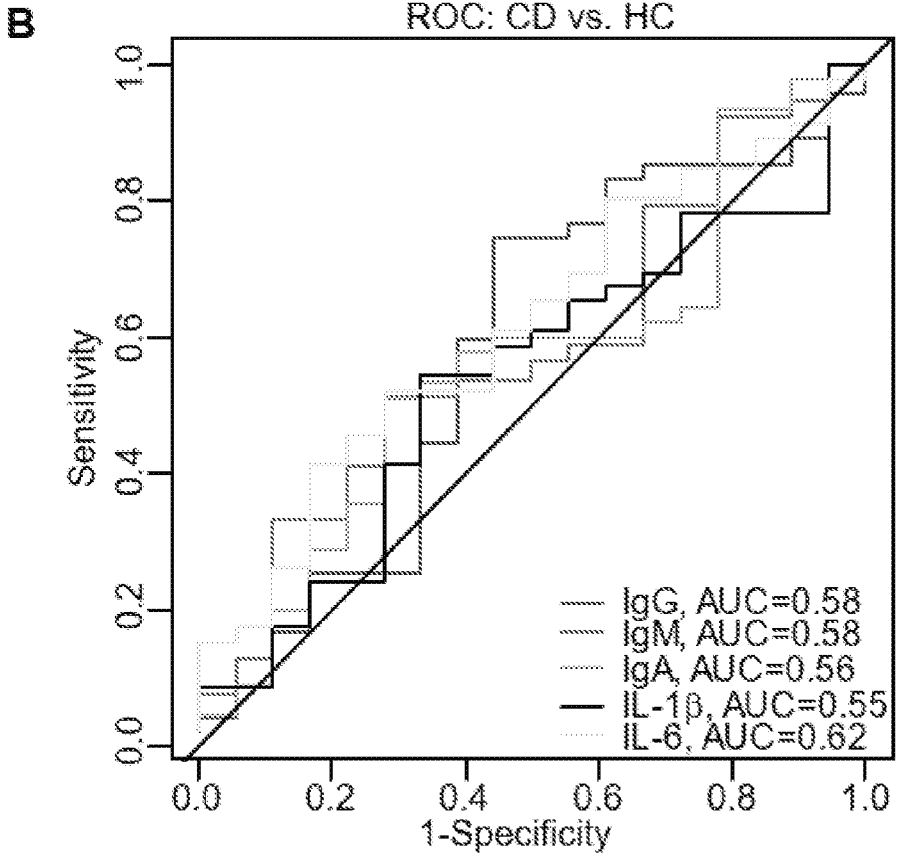
Fig. 7, cont'd.

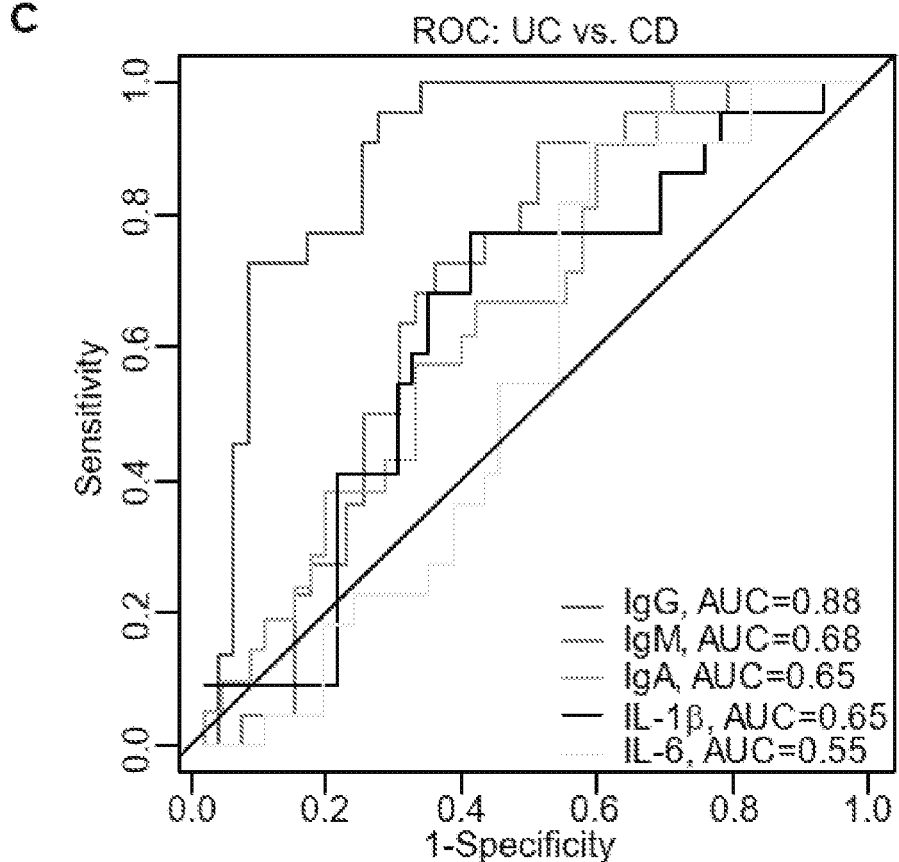
Fig. 7, cont'd.

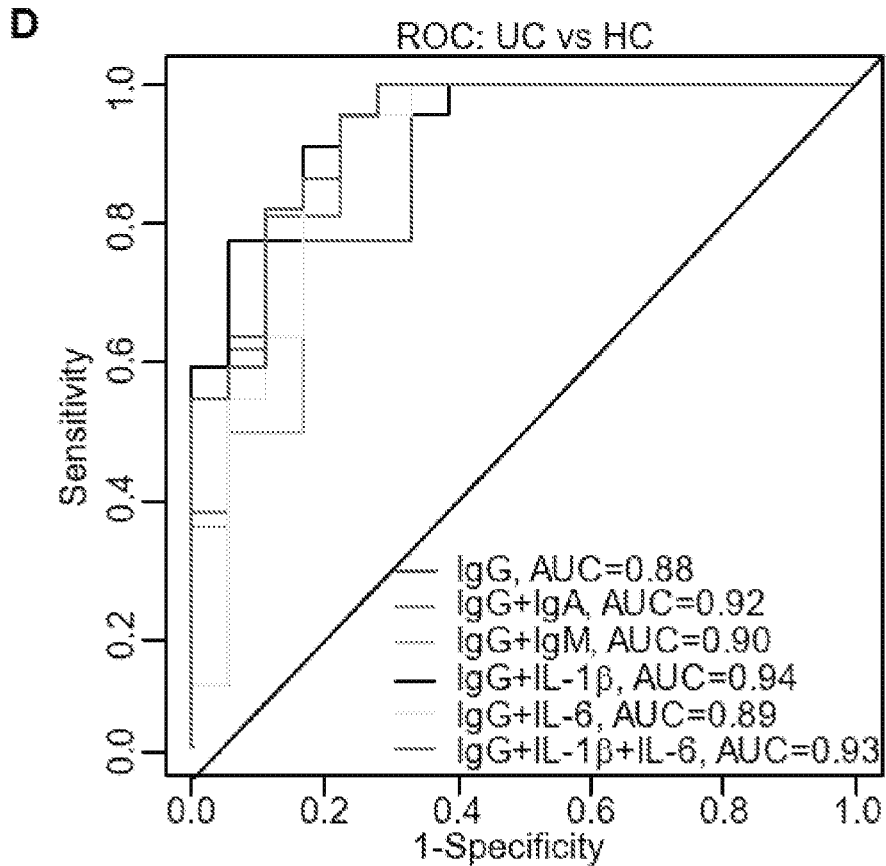
Fig. 7, cont'd.

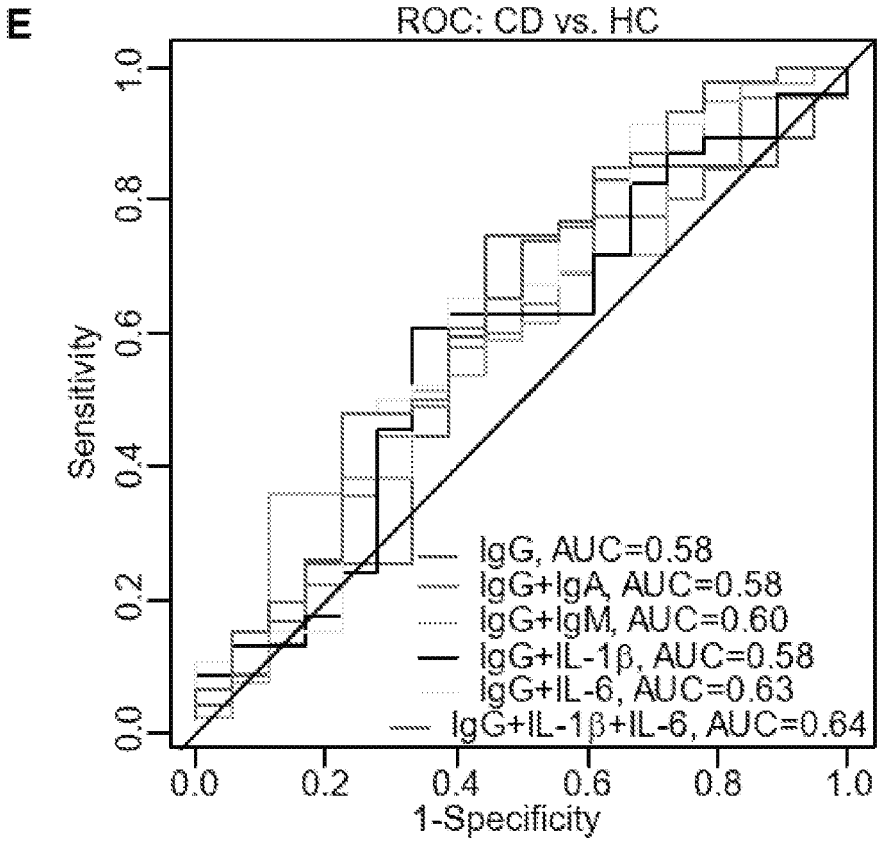
Fig. 7, cont'd.

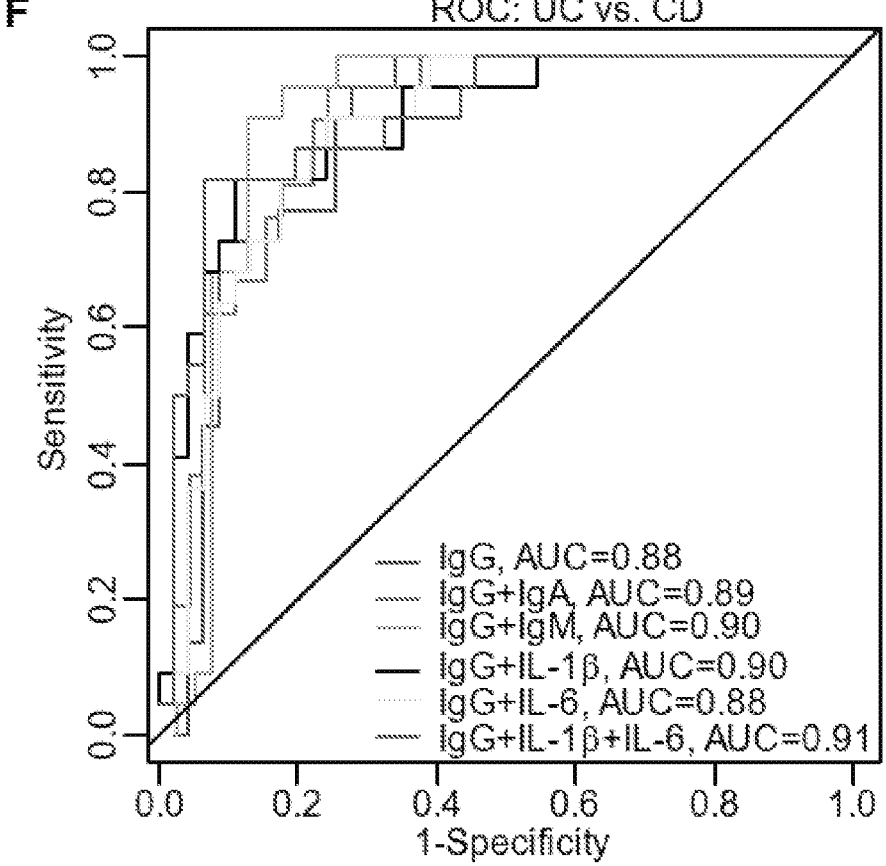
Fig. 7, cont'd.

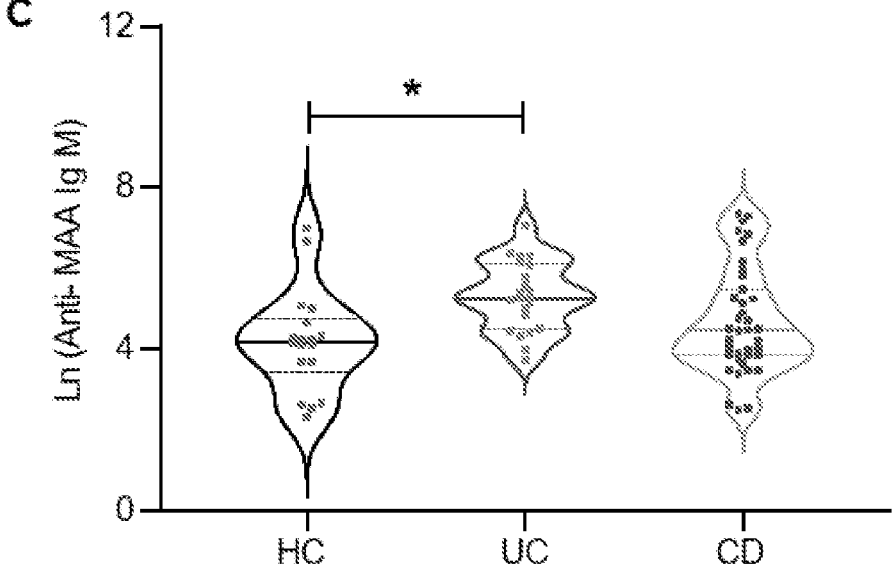
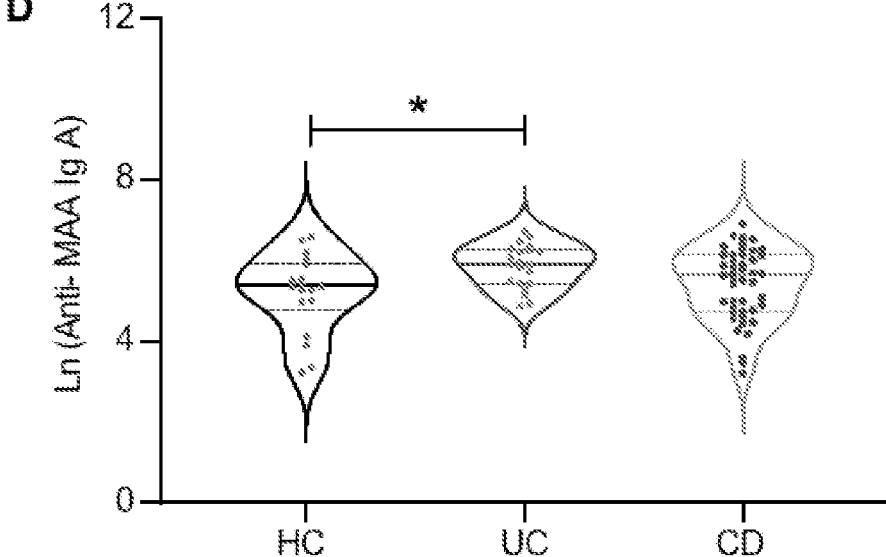
Fig. 8, cont'd.

ANTI-MAA IMMUNOGLOBULIN ISOTYPES IN INFLAMMATORY BOWEL DISEASE: NOVEL DIAGNOSTIC IMPLICATIONS FOR ULCERATIVE COLITIS

CROSS-REFERENCE TO RELATED APPLICATIONS

This application is a U.S. 371 National phase of PCT/US2021/013646, filed on Jan. 15, 2021, which claims benefit of and priority to U.S. Ser. No. 63/081,138, filed on Sep. 21, 2020, and benefit of and priority to U.S. Ser. No. 62/961,372, filed on Jan. 15, 2020, all of which are incorporated herein by reference in their entirety for all purposes.

STATEMENT OF GOVERNMENTAL SUPPORT

Not Applicable

BACKGROUND

Lipid constituents of the biological membranes are the primary targets of the oxidants generated by oxidative stress.[1] Lipid peroxidation has also been highlighted as a critical biological process driving the effects of oxidative stress on disease processes including gut inflammation.[1] Malondialdehyde (MDA) and Acetaldehyde (AA), two highly reactive aldehydes, are the products of lipid peroxidation, which can interact and covalently modify biomolecules we have termed Malondialdehyde-Acetaldehyde (MAA)-Adducts.[2] MAA-adducts also promote inflammatory responses and trigger cytokine secretion such as TNF-$\alpha$, IL-6, and IFN-$\gamma$.[3] Recent studies, including ours, have shown that MAA-adducts may play a critical pathogenic role in the initiation/progression of chronic inflammatory pathologies including, but not limited to; rheumatoid arthritis and cardiovascular disease.[3-6]

Animal studies have shown that MAA-adducts provoke both pro-inflammatory and adaptive T-cell responses, suggesting that MAA may have a causal relationship with immunologic responses in the absence of an adjuvant. Previous studies have further shown that MAA-adducts could generate antibody and T-cell responses to the carrier protein, providing a plausible mechanism by which tolerance to self-proteins is abolished, potentially resulting in autoimmunity.[7,8]

Inflammatory bowel disease (IBD) is a conglomerate of chronic inflammatory disorders of the gut where ulcerative colitis (UC) and Crohn's Disease (CD) are the principal manifestations. The etiology of IBD is uncertain and its proper diagnosis requires a multitude of invasive diagnostic procedures. Beyond being invasive, these diagnostic measures are expensive, uncomfortable and sometimes life threatening. Moreover, due to the potential crossover of the pathobiology and symptoms, clear diagnosis of the UC versus CD is difficult, especially during initial diagnosis.

With uncertain etiology, IBD is characterized by excessive accumulation of immune cells in the gut and induction of complex inflammatory cascades.[9] While, IBD is considered a multi-factorial disease, oxidative stress has been considered a key risk factor.[10] However, status of the MAA-adducts and anti-MAA antibodies in IBD has heretofore remained unclear.

SUMMARY

The studies described herein were undertaken to investigate the status and clinical relevance of MAA-adducts and the antibody response to these adducts in inflammatory bowel disease (IBD). Based on an extensive investigation, it was discovered that antibody responses to the MAA-adducts could be used to discriminate IBD patients from healthy individuals. It was further demonstrated that anti-MAA IgG levels can help differentiate UC from CD including CD involving the colon with high specificity and sensitivity.

Accordingly, various embodiments contemplated herein may include, but need not be limited to, one or more of the following:

Embodiment 1: A method of identifying a mammal having ulcerative colitis, said method comprising:
determining, or causing to be determined, the presence and/or level of antibodies that bind a malondialdehyde acetaldehyde adduct (MAA adduct) in a biological sample from said mammal, where an elevated level of said antibodies, as compared to other forms of colitis, indicates the presence of ulcerative colitis.

Embodiment 2: A method of discriminating between ulcerative colitis and Crohn's disease in said mammal, said method comprising:
determining, or causing to be determined, the level of IgG antibodies that bind a malondialdehyde-acetaldehyde adduct (MAA adduct) in a biological sample from said mammal, where:
an elevated level of said antibodies as compared to the average level found in a mammal with Crohn's disease is an indicator that said mammal has ulcerative colitis rather than Crohn's disease.

Embodiment 3: The method according to any one of embodiments 1-2, wherein said mammal is a mammal that presents with one or more symptoms of inflammatory bowel disease.

Embodiment 4: The method according to any one of embodiments 1-3, wherein said mammal is a mammal known to have or suspected of having inflammatory bowel disease.

Embodiment 5: The method of embodiment 4, wherein said mammal has one or more risk factors selected from the group consisting of relative(s) with IBD, ethnicity, smoking, and age.

Embodiment 6: The method according to any one of embodiments 1-3, wherein said mammal presents with at least 2, or at least 3, or at least 4, or at least 5, or at least 6, or at least 7, or at least 8, or at least 9, or at least 10 symptoms of inflammatory bowel disease.

Embodiment 7: The method according to any one of embodiments 1-6, wherein symptoms of inflammatory bowel disease comprise one or more symptoms selected from the group consisting of diarrhea, fever, fatigue, blood in stool, bleeding ulcers, stomach pain, bloating and cramping, reduced appetite, unintended weight loss, anemia, and flatulence.

Embodiment 8: The method according to any one of embodiments 1-7, wherein the IgG antibodies that bind a MAA adduct are detected as part of a differential diagnosis.

Embodiment 9: The method according to any one of embodiments 1-8, wherein said mammal is a non-human mammal and said biological sample is from said non-human mammal.

Embodiment 10: The method of embodiment 9, wherein said mammal is a cat or dog.

Embodiment 11: The method according to any one of embodiments 1-8, wherein said mammal is a human and said biological sample is from said human

Embodiment 12: The method according to any one of embodiments 1-11, wherein said biological sample comprises a sample selected from the group consisting of whole blood, a blood fraction, saliva/oral fluid, urine, a tissue biopsy, pleural fluid, pericardial fluid, cerebral spinal fluid, and peritoneal fluid.

Embodiment 13: The method of embodiment 12, wherein said sample comprises blood or a blood fraction.

Embodiment 14: The method of embodiment 12, wherein said sample comprises serum.

Embodiment 15: The method according to any one of embodiments 1-14, wherein an anti-MAA adduct IgG antibody is detected in an assay wherein the biological sample is fractionated to separate a fraction comprising said antibody from at least one other sample component.

Embodiment 16: The method according to any one of embodiments 1-15, wherein IgG antibodies that bind an MAA adduct are detected in an assay wherein the antibody and/or a complex formed between the antibody and a MAA adduct becomes labeled with a detectable label.

Embodiment 17: The method according to any one of embodiments 1-16, wherein IgG antibodies that bind an MAA adduct are detected in an assay wherein the antibodies go from an unbound state to a bound state by forming a complex with another assay component.

Embodiment 18: The method according to any one of embodiments 1-17, wherein the anti-MAA IgG antibodies are detected in an assay wherein the antibodies initially present in a soluble phase becomes immobilized on a solid phase.

Embodiment 19: The method according to any one of embodiments 1-18, wherein the level of the IgG antibody is measured using an assay selected from the group consisting of SDS/PAGE, isoelectric focusing, 2-dimensional gel electrophoresis, a hemagglutination assay, and an immunoassay.

Embodiment 20: The method of embodiment 19, wherein the level of IgG antibody is measured using an ELISA assay.

Embodiment 21: The method according to any one of embodiments 19-20, wherein said immunoassay comprises:

providing a MAA adduct immobilized on a solid support;

contacting said MAA adduct with said biological sample under conditions in which anti-MAA adduct antibodies in said sample are bind MAA adduct forming an adduct/antibody complex; and contacting said complex with detection antibodies that specifically bind IgG antibodies, or contacting said complex with a detection reagent that binds any antibody; and detecting and/or quantifying the bound detection antibodies or the bound detection reagent.

Embodiment 22: The method of embodiment 21, wherein:

said detection antibodies are attached to a detectable label or bound by another antibody attached to a detectable label; and/or said detection reagent is attached to a detectable label and/or said detection reagent is bound by an antibody attached to a detectable label; and said quantifying comprises detecting and/or quantifying said detectable label.

Embodiment 23: The method according to any one of embodiments 1-22, wherein the level of said antibodies is significantly elevated compared to the average level found in a healthy mammal of the same species and is an indicator that the mammal has inflammatory bowel disease.

Embodiment 24: The method according to any one of embodiments 1-23, wherein the level of said antibodies is significantly elevated as compared to the average level found in a mammal of the same species with Crohn's disease and is an indicator that said mammal has ulcerative colitis rather than Crohn's disease.

Embodiment 25: The method of embodiment 24, wherein the elevated level of said antibodies is at least 1.2 times, or at least 1.5 times, or at least 1.8 times, or at least 2 times the average level found in a mammal of the same species with Crohn's disease.

Embodiment 26: The method of embodiment 24, wherein the level of said antibodies is significantly elevated at a p value of $p<0.05$ or $p<0.01$.

Embodiment 27: The method of embodiment 24, wherein said elevated level comprises an IgG level of 166.9 or greater as shown in Table 7.

Embodiment 28: The method according to any one of embodiments 24-27, wherein the mammal is further evaluated for ulcerative colitis.

Embodiment 29: The method of embodiment 28, wherein said mammal is administered one or more tests selected from the group consisting of a complete blood count (CBC) to check for anemia, a stool test to check for white blood cells, a colonoscopy to visualize the intestinal tract, a sigmoidoscopy to visualize the rectum and part of colon, an abdominal x-ray to detect perforations in the colon, and a CT scan of the pelvic region.

Embodiment 30: The method according to any one of embodiments 24-29, wherein said mammal is treated for ulcerative colitis.

Embodiment 31: The method of embodiment 30, wherein said treatment comprises prescription of and/or administration of one or more pharmaceutical for ulcerative colitis.

Embodiment 32: The method of embodiment 31, wherein said pharmaceutical comprises one or more drugs selected from the group consisting of anti-inflammatory drugs, corticosteroids, and immunomodulators.

Embodiment 33: The method of embodiment 32, wherein said pharmaceutical comprises an anti-inflammatory drug.

Embodiment 34: The method of embodiment 33, wherein said anti-inflammatory drug comprises a drug selected from the group consisting of sulfasalazinem, olsalazine, and adalimumab.

Embodiment 35: The method according to any one of embodiments 32-34, wherein said pharmaceutical comprises a corticosteroid.

Embodiment 36: The method of embodiment 35, wherein said pharmaceutical comprises a corticosteroid selected from the group consisting of cortisone, Prednisone, Methylprednisolone, Hydrocortisone, and budesonide.

Embodiment 37: The method according to any one of embodiments 32-36, wherein said pharmaceutical comprises an immunomodulator.

Embodiment 38: The method of embodiment 37, wherein said pharmaceutical comprise an immunomodulator selected from the group consisting of mercaptopurine, and azathioprine.

Embodiment 39: The method according to any one of embodiments 30-38, wherein said treatment comprises a surgical procedure used in the treatment of ulcerative colitis.

Embodiment 40: The method of embodiment 39, wherein said surgical procedure comprises a procedure selected from the group consisting of ileoanal anastomosis, proctocolectomy, and colectomy.

Embodiment 41: The method according to any one of embodiments 30-40, wherein said method comprises an alteration in diet of said mammal Embodiment 42: The method of embodiment 41, wherein said alteration of diet comprises avoidance of one or more foods selected from the group consisting of caffeine laden food like tea and coffee, alcoholic drinks, carbonated drinks, foods rich in fiber (e.g., dried beans, fruits, whole grains, berries, peas, and legumes), and foods rich in sulfur or sulfites (e.g., wheat pasta, breads, peanuts, raisins, and cured meats).

Embodiment 43: The method according to any one of embodiments 41-42, wherein said alteration of diet comprises an increase in diet proportion of one or more foods selected from the group consisting of low fiber foods like potatoes, white rice and refined pasta, dairy products like yogurt milk, and cottage cheese, and foods rich in omega 3 fatty acids like walnuts, salmon and mackerel.

Embodiment 44: The method according to any one of embodiments 1-43, wherein the level of said antibodies is not significantly elevated as compared to the level found in a mammal of the same species with Crohn's disease and is an indicator that said mammal has Crohn's disease rather than ulcerative colitis.

Embodiment 45: The method of embodiment 44, wherein the mammal is further evaluated for Crohn's disease.

Embodiment 46: The method of embodiment 44, wherein said mammal is administered one or more tests selected from the group consisting of a complete blood count (CBC) where low red blood cell count indicates anemia, and increased white blood cell count indicates infection or inflammation, a barium swallow to identify the sites affected and assess the severity of the condition, a CT scan of the abdomen to provide more details and to detect other underlying conditions like abscess, and endoscopy to visualize the interior of the intestine.

Embodiment 47: The method according to any one of embodiments 44-46, wherein said mammal is treated for Crohn's disease.

Embodiment 48: The method of embodiment 47, wherein said treatment comprises prescription of and/or administration of one or more pharmaceuticals, nutritional supplements, and surgery either independently or in combination.

Embodiment 49: The method of embodiment 47, wherein said treatment comprises prescription of and/or administration of one or more pharmaceuticals for the treatment of Crohn's disease.

Embodiment 50: The method of embodiment 49, wherein said method comprises prescription of and/or administration of one or more pharmaceuticals.

Embodiment 51: The method of embodiment 50, wherein said one or more pharmaceuticals comprises an anti-inflammatory drug.

Embodiment 52: The method of embodiment 51, wherein said pharmaceutical comprises an anti-inflammatory drug selected from the group consisting of sulfasalazine, mesalamine, and olsalazine.

Embodiment 53: The method according to any one of embodiments 49-52, wherein said one or more pharmaceuticals comprises an immunosuppressant.

Embodiment 54: The method of embodiment 53, wherein said one or more pharmaceuticals comprises an immunosuppressant selected from the group consisting of Azathioprine, and Tacrolimus.

Embodiment 55: The method according to any one of embodiments 49-54, wherein said one or more pharmaceuticals comprise a monoclonal antibody.

Embodiment 56: The method of embodiment 55, wherein said one or more pharmaceuticals comprises a monoclonal antibody selected from the group consisting of Infliximab, Adalimumab, and Certolizumab.

Embodiment 57: The method according to any one of embodiments 49-56, wherein said one or more pharmaceuticals comprises an antibiotic.

Embodiment 58: The method of embodiment 57, wherein said one or more pharmaceuticals comprise an antibiotic selected from the group consisting of Ampicillin, Cefotaxime, Ciprofloxacin, and Tetracycline.

Embodiment 59: The method according to any one of embodiments 49-58, wherein said one or more pharmaceuticals comprises an antidiarrheal agent.

Embodiment 60: The method of embodiment 59, wherein said one or more pharmaceuticals comprises Loperamide.

Embodiment 61: The method according to any one of embodiments 47-60, wherein said treatment comprises one or more surgical procedures.

Embodiment 62: The method of embodiment 61, wherein said surgical procedure comprises a colectomy.

Embodiment 63: The method according to any one of embodiments 47-62, wherein said treatment comprises fluid replacement.

Embodiment 64: The method according to any one of embodiments 47-63, wherein said treatment comprises administration of nutritional supplements selected from the group consisting of iron, vitamin B, calcium and vitamin D Embodiment 65: The method according to any one of embodiments 47-64, wherein said treatment comprises alteration of the diet of the mammal.

Embodiment 66: The method of embodiment 65, wherein said alteration of the diet comprises avoidance of one or more food products selected from the group consisting of spicy foods, foods containing caffeine, dairy products, and processed foods.

Embodiment 67: The method according to any one of embodiments 1-66, wherein the anti-MAA adduct IgG antibody level and/or a diagnosis based, at least in part, on said level is recorded in a patient medical record.

Embodiment 68: The method according of embodiment 67, wherein said patient medical record is maintained by a laboratory, physician's office, a hospital, a health maintenance organization, an insurance company, or a personal medical record website.

Embodiment 69: The method according to any one of embodiments 1-68, wherein a diagnosis, based at least in part on the anti-MAA adduct IgG antibody level is recorded on or in a medic alert article selected from a card, worn article, or radiofrequency identification (RFID) tag.

Embodiment 70: The method according to any one of embodiments 67-69, wherein said antibody levels and/ or a diagnosis based upon the levels of said antibodies is recorded on a non-transient computer readable medium.

Embodiment 71: The method according to any one of embodiments 1-70, wherein said method additionally comprises informing the subject of a result of a determination of anti-MAA adduct IgG antibody assay and/ or of a diagnosis based at least in part on said anti-MAA adduce IgG antibody assay.

Embodiment 72: The method according to any one of embodiments 1-71, wherein the IgG antibodies that bind a MAA adduct are detected as part of a differential diagnosis.

Embodiment 73: The method according to any one of embodiments 1-72, wherein said mammal is a non-human mammal and said biological sample is from said non-human mammal.

Embodiment 74: A method of treating a mammal for inflammatory bowel disease, said method comprising: providing one or more measurements of the level of IgG antibodies that bind a malondialdehyde-acetaldehyde adduct (MAA adduct) in a biological sample from said mammal and:
  where levels of said antibody are significantly higher than the average level of said antibody in a mammal of the same species that has Crohn's disease, treating or causing said mammal to be treated for ulcerative colitis; or
  where levels of said antibody are not significantly higher than the average level of said antibody in a mammal of the same species that has Crohn's disease, treating or causing said mammal to be treated for Crohn's disease.

Embodiment 75: The method of embodiment 74, wherein said providing one or more measurements comprises performing a method according to any one of embodiments 1-22.

Embodiment 76: The method according to any one of embodiments 74-75, wherein levels of said antibody are significantly higher than the average level of said antibody in a mammal of the same species that has Crohn's disease of same species, and said method comprises treating or causing said mammal to be treated for ulcerative colitis.

Embodiment 77: The method of embodiment 76, wherein the elevated level of said antibodies is at least 1.2 times, or at least 1.5 times, or at least 1.8 times, or at least 2 times the average level found in a mammal of the same species with Crohn's disease.

Embodiment 78: The method of embodiment 76, wherein the level of said antibodies is significantly elevated at a p value of $p<0.05$ or $p<0.01$.

Embodiment 79: The method of embodiment 76, wherein said elevated level comprises an IgG level of 166.9 or greater as shown in Table 7.

Embodiment 80: The method according to any one of embodiments 76-79, wherein said treating or causing to be treated comprises prescription of and/or administration of one or more pharmaceutical for ulcerative colitis.

Embodiment 81: The method of embodiment 80, wherein said pharmaceutical comprises one or more drugs selected from the group consisting of anti-inflammatory drugs, corticosteroids, and immunomodulators.

Embodiment 82: The method of embodiment 81, wherein said pharmaceutical comprises an anti-inflammatory drug.

Embodiment 83: The method of embodiment 82, wherein said anti-inflammatory drug comprises a drug selected from the group consisting of sulfasalazinem, olsalazine, and adalimumab.

Embodiment 84: The method according to any one of embodiments 81-83, wherein said pharmaceutical comprises a corticosteroid.

Embodiment 85: The method of embodiment 84, wherein said pharmaceutical comprises a corticosteroid selected from the group consisting of cortisone, prednisone, methylprednisolone, hydrocortisone, and budesonide.

Embodiment 86: The method according to any one of embodiments 81-85, wherein said pharmaceutical comprises an immunomodulator.

Embodiment 87: The method of embodiment 86, wherein said pharmaceutical comprise an immunomodulator selected from the group consisting of mercaptopurine, and azathioprine.

Embodiment 88: The method according to any one of embodiments 76-87, wherein said treatment comprises a surgical procedure used in the treatment of ulcerative colitis.

Embodiment 89: The method of embodiment 88, wherein said surgical procedure comprises a procedure selected from the group consisting of ileoanal anastomosis, proctocolectomy, and colectomy.

Embodiment 90: The method according to any one of embodiments 76-89, wherein said method comprises an alteration in diet of said mammal Embodiment 91: The method of embodiment 90, wherein said alteration of diet comprises avoidance of one or more foods selected from the group consisting of caffeine laden food like tea and coffee, alcoholic drinks, carbonated drinks, foods rich in fiber (e.g., dried beans, fruits, whole grains, berries, peas, and legumes), and foods rich in sulfur or sulfites (e.g., wheat pasta, breads, peanuts, raisins, and cured meats).

Embodiment 92: The method according to any one of embodiments 90-91, wherein said alteration of diet comprises an increase in diet proportion of one or more foods selected from the group consisting of low fiber foods like potatoes, white rice and refined pasta, dairy products like yogurt milk, and cottage cheese, and foods rich in omega 3 fatty acids like walnuts, salmon and mackerel.

Embodiment 93: The method according to any one of embodiments 74-75, wherein levels of said antibody are not significantly higher than the average level of said antibody in a mammal of the same species that has Crohn's disease, and said method comprises treating or causing said mammal to be treated for Crohn's disease.

Embodiment 94: The method of embodiment 93, wherein said treating or causing said mammal to be treated comprises prescription of and/or administration of one or more pharmaceuticals, nutritional supplements, and/or surgery either independently or in combination.

Embodiment 95: The method of embodiment 94, wherein said treating or causing to be treated comprises administration of one or more pharmaceuticals for the treatment of Crohn's disease.

Embodiment 96: The method of embodiment 95, wherein said method comprises prescription of and/or administration of one or more pharmaceuticals.

Embodiment 97: The method of embodiment 96, wherein said one or more pharmaceuticals comprises an anti-inflammatory drug.

Embodiment 98: The method of embodiment 97, wherein said one or more pharmaceuticals comprise an anti-inflammatory drug selected from the group consisting of sulfasalazine, mesalamine, and olsalazine.

Embodiment 99: The method according to any one of embodiments 95-98, wherein said one or more pharmaceuticals comprises an immunosuppressant.

Embodiment 100: The method of embodiment 99, wherein said pone or more pharmaceuticals comprise an immunosuppressant selected from the group consisting of Azathioprine, and Tacrolimus.

Embodiment 101: The method according to any one of embodiments 95-100, wherein said one or more pharmaceuticals comprise a monoclonal antibody.

Embodiment 102: The method of embodiment 95, wherein said one or more pharmaceuticals comprise a monoclonal antibody selected from the group consisting of Infliximab, Adalimumab, and Certolizumab.

Embodiment 103: The method according to any one of embodiments 95-102, wherein said one or more pharmaceuticals comprises an antibiotic.

Embodiment 104: The method of embodiment 95-103, wherein said one or more pharmaceuticals comprise an antibiotic selected from the group consisting of Ampicillin, Cefotaxime, Ciprofloxacin, and Tetracycline.

Embodiment 105: The method according to any one of embodiments 95-104, wherein said one or more pharmaceuticals comprises an antidiarrheal agent.

Embodiment 106: The method of embodiment 105, wherein said one or more pharmaceuticals comprises Loperamide.

Embodiment 107: The method according to any one of embodiments 93-106, wherein said treating or causing to be treated comprises providing one or more surgical procedures.

Embodiment 108: The method of embodiment 107, wherein said surgical procedure comprises a colectomy.

Embodiment 109: The method according to any one of embodiments 93-108, wherein said treating or causing to be treated comprises fluid replacement.

Embodiment 110: The method according to any one of embodiments 93-109, wherein said treating or causing to be treated comprises administration of nutritional supplements selected from the group consisting of iron, vitamin B, calcium and vitamin D Embodiment 111: The method according to any one of embodiments 93-110, wherein said treating or causing to be treated comprises alteration of the diet of the mammal.

Embodiment 112: The method of embodiment 111, wherein said alteration of the diet comprises avoidance of one or more food products selected from the group consisting of spicy foods, foods containing caffeine, dairy products, and processed foods.

Definitions

The term "biological sample" or "test sample" refers to sample is a sample of biological tissue, cells, or fluid that, in a healthy and/or pathological state, contains an analyte that is to be detected, e.g., an antibody reactive to a MAA protein adduct (e.g., an anti-MAA adduct IgG). Such samples include, but are not limited to sputum/oral fluid, amniotic fluid, blood, a blood fraction, or fine needle biopsy samples (e.g., surgical biopsy, fine needle biopsy, etc.) urine, peritoneal fluid, pleural fluid, and the like. Although the sample is typically taken from a human subject (e.g., patient), the assays can be used to detect anti-MAA adduct antibodies in samples from any mammal, such as dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, inactivation of interfering components, the addition of reagents, lysing, etc. If such methods of pretreatment are employed with respect to the sample, such pretreatment methods are typically such that the analyte of interest (e.g., anti-MAA adduct antibodies) remains in the test sample, preferably at a concentration proportional to that in an untreated test sample (e.g., namely, a sample that is not subjected to any such pretreatment method(s)). Such "treated" or "processed" samples are still considered to be biological samples with respect to the methods described herein.

The term "blood" includes whole blood, or blood fractions such as serum or plasma.

By "diagnostic test" is meant any kind of medical test performed to aid in the diagnosis or detection of disease and/or pathology.

An antibody when used with respect to an analyte that is to be detected in a diagnostic/prognostic assay as described herein (e.g., an anti-MAA protein adduct antibody) refers to an endogenous (endogenously generated antibody). The antibody typically comprises one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An antibody when used with respect to a targeting moiety used for the detection of a particular antigen (e.g., MAA adduct) refers to a full (intact immunoglobulin) or any of a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region thereby converting the $(Fab')_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies also include single chain antibodies (antibodies that exist as a single polypeptide chain), e.g., single chain Fv antibodies (sFv or scFv) in which a variable heavy and a variable light chain are joined together (directly or through a peptide linker) to form a continuous polypeptide. The single chain Fv antibody is typically a covalently linked $V_H$-$V_L$ heterodimer which may be expressed from a nucleic acid including $V_H$- and $V_L$-encoding sequences either joined directly or joined by a peptide-encoding linker (see, e.g., Huston, et al. (1988) *Proc. Nat. Acad. Sci.* USA, 85: 5879-5883).

An "MAA adduct" refers to any macromolecule modified with the MAA moiety as previously described (see, e.g., Hill et al. (1998) Atherosclerosis, 141: 107-116, U.S. Pat. No. 5,939,535, and the like). An "MAA protein adduct" refers to a protein modified with the MAA moiety.

An "anti-MAA adduct antibody" or "anti-MAA protein adduct antibody" refers to an antibody that specifically binds to (e.g., is reactive with) a MAA protein adduct. The MAA protein adduct can be one that is naturally occurring in a mammal, or one that is synthetically produced.

A "risk factor" is a factor identified to be associated with an increased risk. A risk factor for ulcerative colitis or Crohn's disease is any factor identified to be associated with an increased risk of developing those conditions or of worsening those conditions. A risk factor can also be associated with an increased risk of an adverse clinical event or an adverse clinical outcome in a patient with ulcerative colitis or Crohn's disease. Illustrative risk factors for ulcerative colitis and Crohn's disease include, but are not limited to age, race or ethnicity, and family history. In this regard it is noted that ulcerative colitis usually begins before the age of 30, but it can occur at any age, while Crohn's disease affects people primarily between 15 and 30 years of age or between 60 and 80 years of age. With respect to race or ethnicity, it is noted that although whites have the highest risk of the diseases, they can occur in any race, however risk is increased in Ashkenazi Jews. With respect to family history risk is increased if a close relative (parent, sibling, or child) has the disease. Additional risk factors for Crohn's disease include, but are not limited to cigarette smoking, psychosocial factors (e.g., major stressful life events such as illness or death in family, divorce, separation, interpersonal conflict, or other major loss), medications (e.g., non-Steroidal anti-inflammatory medications such as ibuprofen, naproxen sodium, diclofenac sodium and others), and living conditions (e.g., living in an urban area or in an industrialized country), and diet (e.g., diet high in fat or refined foods).

The term "treating" as used herein is intended to encompass curing as well as ameliorating at least one symptom of a disease or at least one abnormality associated with a disorder. For example, in certain embodiments treating ulcerative colitis can take place by administering a pharmaceutical useful in the treatment of ulcerative colitis. Treating ulcerative colitis or Crohn's disease can also take place by modifying risk factors that are related to ulcerative colitis or Crohn's disease.

As used herein, the terms "subject" and "patient" are used interchangeably irrespective of whether the subject has or is currently undergoing any form of treatment. As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous monkey, chimpanzee, etc.) and a human) In certain embodiments the subject is a human.

When it is said that the level of a particular marker (e.g., anti-MAA adduct antibody) is an "indicator" of a particular pathology or prognosis it is not intended to suggest that the presence or level of the marker is dispositive for that pathology or prognosis. Rather the indicator is intended to be used in the context of other information (e.g., in the context of a differential diagnosis) to inform further testing and/or evaluation, and/or lifestyle/behavioral changes, and/or to inform further treatment or alteration in treatment regimen.

The phrase "cause to be administered" refers to the actions taken typically by a medical professional (e.g., a physician), or a person controlling medical care of a subject, that control and/or permit the administration of the agent(s) at issue to the subject. Causing to be administered can involve diagnosis and/or determination of an appropriate therapeutic or prophylactic regimen, and/or prescribing particular agent(s) for a subject. Such prescribing can include, for example, drafting a prescription form, annotating a medical record, and the like.

The term "elevated" when used with reference to a parameter (e.g., anti-MAA IgG antibody level) indicates that the parameter falls within a range that would be recognized as elevated with respect to a reference value (or reference values) by one of ordinary skill in the art. In certain embodiments the reference value can be a value determined for the subject at a previous point in time. In certain embodiments the reference value(s) can be values know or determined for a particular population or subpopulation (e.g., a subpopulation characterized by one or more factors selected from the group consisting of gender, age, ethnicity, weight, health status, and the like). In certain embodiments a parameter is identified as elevated if it falls in a top 25 percentile, or a top 10 percentile, or a top 5 percentile, or a top 2 percentile, or a top 1 percentile of the value for a particular reference population. In certain embodiments the elevated level is a level at least 1.2 time, or at least 1.5 times, or at least 2 times, or at least 5 times, or at least 10 times the level of the reference value. In certain embodiments the parameter is identified as elevated when the level is a statistically significant elevation at ≥95% confidence level, preferably at ≥98% confidence level, more preferably at ≥99% confidence level with respect to the reference level using any appropriate parametric (e.g., ANOVA, t-test, and the like) or non-parametric test.

DETAILED DESCRIPTION

Figure 1:
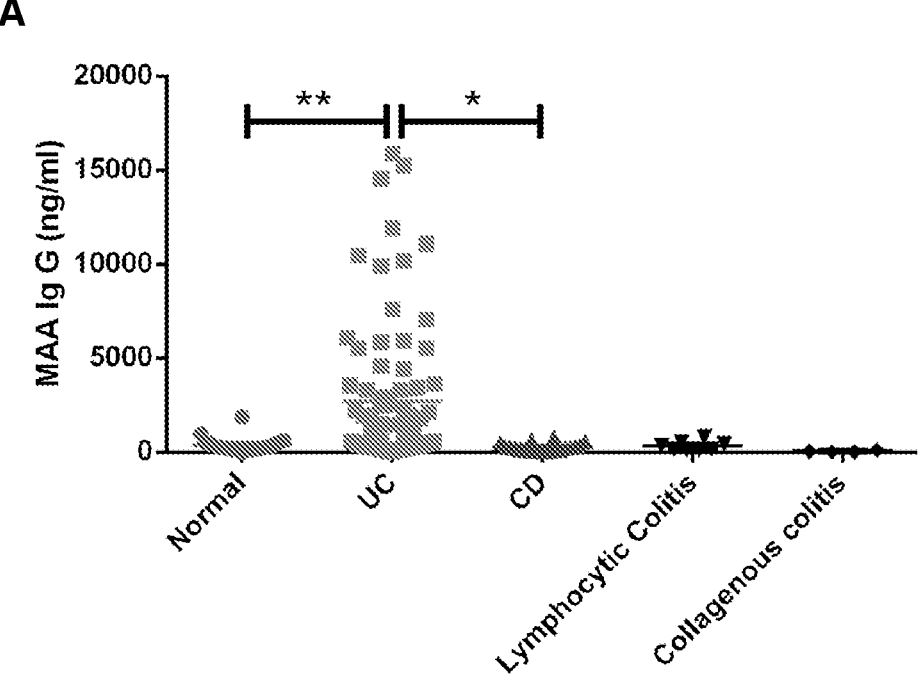
FIG. 1, panels A-C, shows data from the analysis of anti-MAA antibodies for their diagnostic value in differentiating UC versus CD. Panel A) anti-MAA IgG. Panel B) Anti-MAA IgA. Panel C) Anti-MAA IgM.
Figure 1:
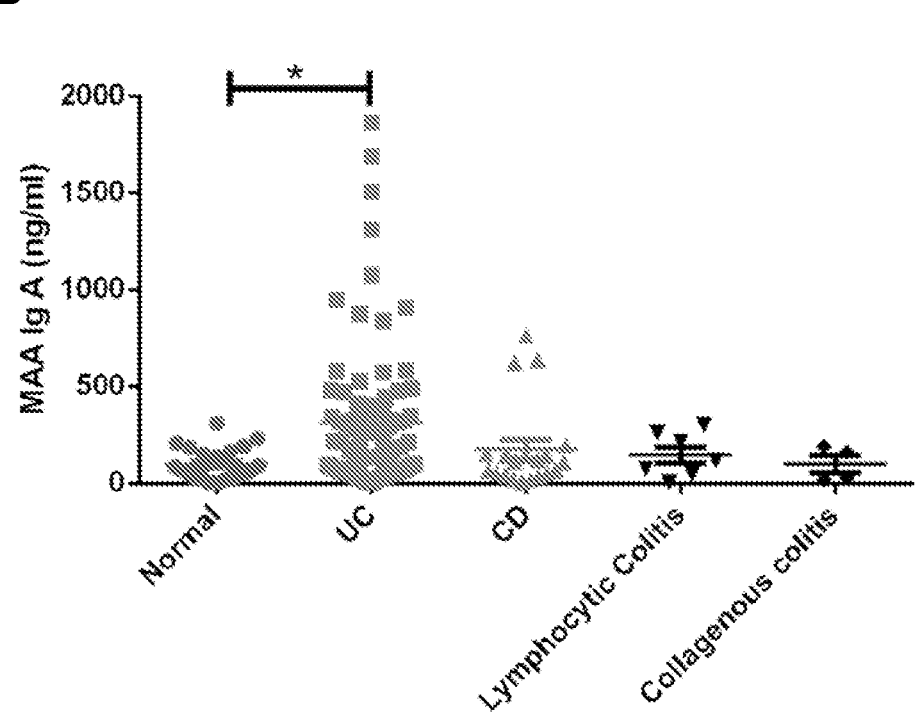

Inflammatory bowel disease (IBD) is a conglomerate of chronic inflammatory disorders of the gut where ulcerative colitis (UC) and Crohn's Disease (CD) are the principal manifestations. The etiology of IBD is uncertain and its proper diagnosis requires a multitude of invasive diagnostic procedures. Beyond being invasive, these diagnostic measures are expensive, uncomfortable and sometimes life threatening. Moreover, due to the potential crossover of the pathobiology and symptoms, clear diagnosis of the UC versus CD is difficult, especially during initial diagnosis. In various embodiments, noninvasive and reliable diagnostic biomarkers are provided that can be effectively used to discriminate ulcerative colitis from Crohn's disease.

Malondialdehyde (MDA), a lipid peroxidation product, is a naturally occurring highly reactive compound implicated in promoting autoimmunity and inflammation. MDA breaks down to form acetaldehyde (AA), which combines with MDA to form a unique MDA-AA adduct (MAA). MAA is highly stable and induces immunogenic reactions even in the absence of adjuvant, and result in adaptive immune responses to the carrier protein itself, thus bypassing tolerance. Considering the recent reports that increased MAA levels correlates with certain autoimmune pathobiology, we examined whether anti-MAA antibodies can also serve as non-invasive biomarkers for the IBD.

It was discovered that anti-MAA IgG is significantly elevated in subjects that present with inflammatory bowel disease. Moreover, it was a surprising discovery that elevated anti-MAA IgG can be used to effectively discriminate between two principal types of inflammatory bowel disease: 1) Crohn's disease, and 2) Ulcerative colitis. In particular, it was discovered that the anti-MAA IgG serotype antibody is significantly higher in subjects with ulcerative colitis (UC) as compared to subjects with Crohn's disease (CD) (see, e.g., FIG. 3).

Accordingly, it is believed that determination of anti-MAA IgG antibodies in a biological sample obtained from a mammal (e.g., a serum sample) can provide an indicator that is useful in determining whether the IBD is ulcerative colitis or Crohn's disease and thereby indicating an appropriate treatment regimen. Accordingly, in certain embodiments, diagnostic methods are provided. Thus, for example, in certain embodiments a method of identifying a mammal having ulcerative colitis is provided where the method comprises determining, or causing to be determined, the presence and/or level of antibodies that bind a malondialdehyde acetaldehyde adduct (MAA adduct) in a biological sample from said mammal, where an elevated level of said antibodies, as compared to other forms of colitis, indicates the presence of ulcerative colitis. In certain embodiments a method of discriminating between ulcerative colitis and Crohn's disease in a mammal is provided where the method comprises determining, or causing to be determined, the level of IgG antibodies that bind a malondialdehyde-acetaldehyde adduct (MAA adduct) in a biological sample from the mammal, where an elevated level of anti-MAA IgG antibodies as compared to the average level found in a mammal with Crohn's disease is an indicator that the mammal has ulcerative colitis rather than Crohn's disease.

In certain embodiments treatment methods are provided. For example, in certain embodiments, a method of treating a mammal for inflammatory bowel disease is provided where the method comprises providing one or more measurements of the level of IgG antibodies that bind a malondialdehyde-acetaldehyde adduct (MAA adduct) (anti-MAA IgG) in a biological sample from the mammal and:

1) where levels of said antibody are significantly higher than the average level of the anti-MAA IgG in a mammal of the same species that has Crohn's disease, treating or causing the mammal to be treated for ulcerative colitis; or 2) where levels of the anti-MAA IgG antibody are not significantly higher than the average level of said antibody in a mammal of the same species that has Crohn's disease, treating or causing the mammal to be treated for Crohn's disease.

In various embodiments, the mammal will be a mammal that presents with one or more symptoms of inflammatory bowel disease. Typical symptoms of inflammatory bowel disease include, but are not limited to diarrhea, fever, fatigue, blood in stool, bleeding ulcers, stomach pain, bloating and cramping, reduced appetite, unintended weight loss, anemia, flatulence.

Inflammatory bowel disease (IBD) is a group of inflammatory conditions of the colon and small intestine and Crohn's disease and ulcerative colitis are the principal types of inflammatory bowel disease. Crohn's disease affects the small intestine and large intestine, as well as the mouth, esophagus, stomach and the anus, whereas ulcerative colitis primarily affects the colon and the rectum. IBD also occurs in dogs, cats, and other non-human mammals and is thought to arise from a combination of host genetics, intestinal microenvironment, environmental components and the immune system.

Diagnosis of IBD often begins by measurement of fecal calprotectin which may suggest the possibility of IBD, as this test is sensitive but not specific for IBD. Accordingly, measurement of fecal calprotectin in combination with determination of anti-MAA IgG as described herein can provide a more definitive diagnosis. In certain embodiments this can be confirmed by biopsies on colonoscopy.

As noted above, discrimination Crohn's disease from ulcerative colitis has heretofore been challenging often requiring rather invasive procedures. Moreover, additional diagnostic tests, treatment methods, and outcomes under various therapeutic regimen differ significantly between the two conditions. Thus, for example, illustrative treatment differences between and outcomes Crohn's disease and ulcerative colitis are shown in Table 1.

TABLE 1

| Illustrative treatment differences between Crohn's disease and ulcerative colitis. | | |
| --- | --- | --- |
| | Crohn's disease | Ulcerative colitis |
| Mesalazine | Less useful | More useful |
| Antibiotics | Effective in long-term | Generally not useful |
| Surgery - Removal of affected part of colon | Often returns following | Usually cured by removal |

In view of these considerations, assessment of anti-MAA IgG can guide the selection of additional test, e.g., to facilitate a differential diagnosis, and/or to inform the therapeutic regimen to be applied.

Thus, for example, common tests and procedures for diagnosing Crohn's disease include, but are not limited to:
1) A physical examination to check for possible causes of the symptoms;
2) A complete blood count (CBC), where a low red blood cell count typically indicates anemia, and increased white blood cell count indicates infection or inflammation;
3) A barium swallow to identify the sites affected and assess the severity of the condition;
4) A CT scan of the abdomen to provide more details and help in detecting any other under lying conditions like abscess, which X-rays might not detect; and/or
5) Endoscopy to provide a detailed view of the inside of intestine.

Common tests and procedures for diagnosing ulcerative colitis include, but are not limited to:
1) A complete blood count (CBC) to check for anemia;
2) A stool test to rule out other disease conditions caused by microbes, infections and parasites;
3) A colonoscopy t examine the extent of damage;
4) A sigmoidoscopy to examine the rectum and part of colon;
5) An abdominal X-ray taken to identify any puncture in the colon; and/or
6) A CT scan to provides detailed images of the pelvic region.

Accordingly, In certain embodiments determination of anti-IgG antibody levels may precede any of these common tests and indicate which tests are further warranted. In certain embodiments determination of anti-IgG antibody levels may be done in conjunction of with any one or more of these common tests inform additional diagnostic testing. In any case, determination of anti-IgG antibody levels can form in important component and indicator in the differential diagnosis of Crohn's disease and/or ulcerative colitis, and in particular, facilitate discrimination of these two conditions.

As noted above, determination of anti-IgG antibody can form an important component of a treatment method for inflammatory bowel disease. In particular, where levels of anti-MAA IgG are significantly higher than the average level of the anti-MAA IgG in a mammal of the same species that has Crohn's disease the mammal is treated for ulcerative colitis, or where levels of the anti-MAA IgG antibody are not significantly higher than the average level of anti-MAA IgG antibody in a mammal of the same species that has Crohn's disease the mammal is treated for Crohn's disease.
Treatment Treatment of Crohn's Disease Treatment of Crohn's disease includes medications, nutritional supplements, and surgery, either independently or in combination. Treatment options depend on the location and severity of the disease.

Medication

Illustrative medications for the treatment of Crohn's disease include, but are not limited to anti-inflammatory drugs (e.g., sulfasalazine, mesalamine, olsalazine, etc.) to reduce inflammation, immunosuppressants (e.g., azathioprine, tacrolimus, etc.) to reduce the immune reaction, monoclonal antibodies (e.g., infliximab, adalimumab, certolizumab, vendolizumab, etc.) for immunosuppression, antibiotics (e.g., ampicillin, cefotaxime, ciprofloxacin, tetracycline, etc.) to control infection, and/or antidiarrheal agents (e.g., loperamide).

Surgical Procedures

Colectomy to remove the severely damaged portions of the intestine is a common treatment for Crohn's disease.

Dietary Modification—Nutrition and Supplements

Modification of diet is frequently indicated in the treatment of Crohn's disease. Such modifications include, but are not limited to eating small meals, drinking large quantities of fluids, increase the amount of whole fresh foods in the diet and inclusion of low-fat foods in the diet. Dietary modifications can also include avoidance or reduction of any foods that worsen symptoms, spicy foods, foods containing caffeine such as tea and coffee, dairy products, and/or processed foods.

Nutritional supplements to replace lost nutrients, including iron, vitamin B, calcium and vitamin D supplements are often indicated.

Treatment of Ulcerative Colitis

Treatment of Ulcerative colitis disease includes medications, surgery, and nutritional modifications either independently or in combination Medication Illustrative medications for the treatment of Crohn's disease include, but are not limited to anti-inflammatory drugs (e.g., sulfasalazine, mesalamine, olsalazine, etc.) to reduce inflammation, corticosteroids (e.g., cortisone, prednisone, methylprednisolone, hydrocortisone, and budesonide) for symptomatic relief, and/or immunomodulators (e.g., mercaptopurine, azathioprine, etc.) to reduce immune system responses that trigger inflammation.

Surgical Procedures

Surgical procedures for the treatment of ulcerative colitis include, but are not limited to ileoanal anastomosis where the lining of the rectum is removed and the small intestine is connected to the anus, proctocolectomy where the large intestine is removed and the small intestine is connected to the anus, and colectomy.

Dietary Modification

In various embodiments dietary modification can include increase of dietary component of low fiber foods like potatoes, white rice and refined pasta, dairy products like yogurt milk, and cottage cheese, and/or foods rich in omega 3 fatty acids like walnuts, salmon and mackerel. In certain embodiments dietary modification can include avoidance or reduction of caffeine laden food like tea and coffee, alcoholic drinks, carbonated drinks, foods rich in fiber dried beans, fruits, whole grains, berries, peas, and legumes, foods rich in sulfur or sulfites wheat pasta, breads, peanuts, raisins, and cured meats, and/or spicy and fatty food.

It will be recognized that the treatment protocols described above are illustrative and non-limiting and determination of anti-MAA IgG level can inform these and any other treatment protocols used for the treatment of Crohn's disease or ulcerative colitis.

Detection/Quantitation of Anti-MAA Adduct IgG Antibodies in a Biological Sample

As described above, the level of anti-MAA IgG antibodies in a subject (e.g., a human or a non-human mammal) provides an indicator that discriminates between Crohn's disease and ulcerative colitis.

Assay methods to detect anti-MAA adduct IgG antibodies in a sample from a subject can be carried out in any of a wide variety of formats. In certain embodiments the subject's levels of IgG antibodies with reactivity to the MAA adduct can be assessed using immunoassays. Immunoassay formats are preferred, e.g., selected from the group consisting of, an immunoblot, a Western blot, a dot blot, an enzyme linked immunosorbent assay (ELISA), radioimmunoassay (RIA), enzyme immunoassay. Modified immunoassays utilizing fluorescence resonance energy transfer (FRET), biosensor technology, evanescent fiber-optics technology, protein chip technology, and the like are also useful. In certain embodiments the assay is a semi-quantitative assay or quantitative assay.

Examples of suitable immunoassays are described below and will, in view of the teachings provided herein, be apparent to those skilled in the art. For a general review of immunoassays, see Methods in Cell Biology Volume 37: Antibodies in Cell Biology, Asai, ed. Academic Press, Inc. New York (1993); Basic and Clinical Immunology 7th Edition, Stites & Terr, eds. (1991), which is incorporated by reference in its entirety.

Immunoassays can be competitive or noncompetitive. In a typical competitive immunoassay, the antibody in the sample competes with labeled antibody to bind with the MAA protein adduct. The amount of labeled antibody bound to the MAA protein conjugate is then measured. There is an inverse relationship between concentrations of endogenous anti-MAA adduct antibody in the sample and the quantity of labeled antibody detected.

In noncompetitive immunoassays, antibody in the sample is bound to the PAF conjugate, then a labeled detection reagent, typically an anti-immunoglobulin antibody, is bound to the antibody. The amount of labeled detection reagent bound to the antibody is then measured. Unlike the competitive method, the results of the noncompetitive method will be directly proportional to the concentration of the antibody.

In a noncompetitive immunoassay or western blot, a labeled detection reagent, typically an anti-immunoglobulin antibody, is used to detect antibody (e.g., anti-MAA adduct IgG antibody) bound to the MAA protein adduct. A suitable anti-immunoglobulin antibody is chosen that binds specifically to immunoglobulin of the species from which the sample is obtained. In certain embodiments it may bind to all IgG immunoglobulin subtypes of that species. In certain embodiments the anti-immunoglobulin antibody may bind specifically only to certain subtypes of IgG. Subtypes of human IgG include IgG1, IgG2, IgG3 and IgG4. In certain embodiments the anti-immunoglobulin may bind to one or more of these human IgG subtypes. It will be appreciated that there are different isotypes and subtypes in different vertebrate species.

In radioimmunoassay, the antibody or detection reagent is labeled with a radioisotope, such as $^{131}$I or $^{125}$I. In enzyme immunoassays, the antibody or detection reagent is labeled with an enzyme. In certain embodiments suitable enzymes are capable of being detected with the use of a chromogenic substrate. A chromogenic substrate is a substance which, as a result of the reaction with the enzyme, gives rise to a colored product which can thus be detected spectrophotometrically. Enzymes such as horse radish peroxidase, alkaline phosphatase, beta-galactosidase, and pyrophosphatase from E. coli have been widely employed. Chemiluminescent systems based on enzymes such as luciferase can also be used. Other labels include fluorescent labels such as fluorophores of the Alexa series, quantum dots, electron spin labels, magnetic labels, and the like. In certain embodiments conjugation of the antibody or detection reagent with the biotin is frequently used since this can readily be detected by its reaction with enzyme- or fluorophore-linked avidin or streptavidin to which it binds with great specificity and affinity. Alternatively, in certain embodiments, the antibody/detection reagent is conjugated with streptavidin or avidin that binds a detection reagent linked biotin.

In one illustrative and typical noncompetitive enzyme immunoassay, the sample to be analyzed (e.g., serum) is placed in contact and incubated with a MAA protein adduct (e.g., a MAA/albumin adduct) adsorbed on (or chemically linked to) a solid (or substantially solid) substrate. Any anti-MAA adduct antibodies that are possibly present in the sample are thus specifically bound by the MAA adduct attached to the solid substrate, producing a MAA adduct/anti-MAA adduct antibody complex. The sample is then separated from the solid substrate so as to eliminate nonbound materials, for example, by washing. An indicator antibody capable of binding anti-MAA adduct IgG antibodies that are present on the substrate in the form of a MAA adduct/anti-MAA adduct antibody complex is added to the solid substrate, thus producing a MAA adduct/anti-MAA adduct antibody/indicator antibody complex. The indicator antibody may, for example, be an anti-human IgG immunoglobulin raised in a non-human animal species. Finally, the presence of the MAA adduct/anti-MAA adduct antibody/indicator antibody complex on the solid substrate is detected and/or quantified, the presence of said complex on the solid substrate being indicative of the presence of anti-MAA protein adduct antibodies in the sample and the amount of the complex being indicative of the amount of anti-MAA protein adduct antibodies in the sample.

In certain embodiments it is preferred that a quantitative estimate of antibody that can bind to the MAA adduct is obtained. In typical non-competitive assays, a linear relationship between the measured variable, whether it be optical density or some other read-out, and antibody concentration, is assumed. For example, if sample A has double the optical density of sample B in the assay (background having been subtracted from both), it is assumed that the concentration of antibody is double in A compared to B. However, it is preferable to construct a standard curve of serial dilutions of a pool of positive samples (e.g., serum samples). In certain embodiments such dilutions are assayed at the same time as the test samples. By doing this, any variation from the linear relationship may be taken into account in determining the quantity of antibody in the samples.

In certain embodiments the solid substrate is a microtitration plate, for example, of the type commonly used for performing ELISA immunological assays. In certain embodiments the micro-titration plate is preferably a polystyrene plate. Useful solid supports also include, but are not limited to natural polymeric carbohydrates and their synthetically modified, crosslinked, or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a preexisting natural polymer. All of these materials may be used in suitable shapes, such as films, sheets, tubes, particulates, or plates, or they may be coated onto, bonded, or laminated to appropriate inert carriers, such as paper, glass, plastic films, fabrics, or the like.

Illustrative solid phase materials well suited for flowthrough assay devices include, but are not limited to filter paper such as a porous fiberglass material or other fiber matrix materials. The thickness of such material is not critical and will be a matter of choice, largely based upon the properties of the sample or analyte being assayed, such as the fluidity of the biological sample.

In certain embodiments the solid phase can constitute microparticles (or nanoparticles). Suitable microparticles useful in the methods described herein can be selected by one skilled in the art from any suitable type of particulate material and include, but are not limited to those composed of polystyrene, polymethylacrylate, polypropylene, latex, polytetrafluoroethylene, polyacrylonitrile, polycarbonate, or similar materials. Further, the microparticles can be magnetic or paramagnetic microparticles, so as to facilitate manipulation of the microparticle within a magnetic field.

Microparticles can be suspended in the mixture of soluble reagents and biological sample or can be retained and immobilized by a support material. In the latter case, the microparticles on or in the support material are typically or preferably not capable of substantial movement to positions elsewhere within the support material. Alternatively, the microparticles can be separated from suspension in the mixture of soluble reagents and biological sample by sedimentation or centrifugation. When the microparticles are magnetic or paramagnetic the microparticles can be separated from suspension in the mixture of soluble reagents and biological sample by a magnetic field.

The methods described herein can be adapted for use in systems that utilize microparticle technology including automated and semi-automated systems wherein the solid phase comprises a microparticle. Such systems include those described in pending U.S. application Ser. No. 425,651 and U.S. Pat. No. 5,089,424, which correspond to published EPO App. Nos. EP 0 425 633 and EP 0 424 634, respectively, and U.S. Pat. No. 5,006,309.

Thus, for example, it will be appreciated that the illustrative assay described above, can also be performed in a fluid phase. The MAA protein adduct can be provided attached to microparticles or nanoparticles that are contacted with the sample in a suspension. Anti-MAA adduct antibodies present in the sample bind to the MAA protein adduct on the microparticles forming a MAA adduct/anti-MAA adduct antibody complex on the surface of the microparticles. This complex is then contacted with an indicator antibody capable of binding anti-MAA adduct antibodies that are present in the MAA adduct/anti-MAA adduct antibody complex thus producing a MAA adduct/anti-MAA adduct antibody/indicator antibody complex attached to the microparticles. The microparticles can then be separated and the label detected/quantified using for example a cell sorter, or a magnetic separation system.

In certain embodiments, the solid substrate can comprise one or more electrodes. The MAA protein adduct (capture agent) can be affixed, directly or indirectly, to the electrode(s). In one embodiment, for example, the MAA protein adduct can be affixed to magnetic or paramagnetic microparticles, which are then positioned in the vicinity of the electrode surface using a magnet. Systems in which one or more electrodes serve as the solid phase are useful where detection is based on electrochemical interactions. Illustrative systems of this type are described, for example, in U.S. Pat. No. 6,887,714. The basic method is described further below with respect to electrochemical detection.

As indicated above, in various embodiments, the MAA-protein adduct can be attached to the solid support (e.g., ELSA well, microparticle, test strip, etc.) by any of a number of methods. The attachment can be simple adsorption, ionic bonding, or covalent coupling (directly or through a linker). In one illustrative embodiment, the MAA adduct is adsorbed to the solid substrate by incubating the MAA adduct in a buffer with the solid substrate. Suitable buffers include, but are not limited to carbonate buffer or phosphate buffered saline. Typically, after adsorption or covalent linkage of the MAA adduct to the solid substrate, the solid substrate is incubated with a blocking agent to reduce non-specific binding of matter from the sample to the solid substrate. Suitable blocking agents include, but are not limited to bovine serum albumin.

In certain embodiments the intrinsic charge of the solid substrate is altered to facilitate attachment of the MAA adduct, and/or to improve antibody binding, and/or to improve wettability, and the like. In certain embodiments to change or enhance the intrinsic charge of the solid substrate, a charged substance can be coated directly onto the substrate. For example, ion capture procedures for immobilizing an immobilizable reaction complex with a negatively charged polymer, described in EP Patent Publication No. 0326100, and in EP Publication No. 0406473, can be employed to affect a fast solution-phase immunochemical reaction. In these procedures, an immobilizable immune complex is separated from the rest of the reaction mixture by ionic interactions between the negatively charged polyanion/immune complex and the previously treated, positively charged matrix and detected by using any of a number of signal-generating systems, including, e.g., chemiluminescent systems, as described in EPO Publication No. 0 273, 115.

If the solid substrate is silicon or glass, the surface is often activated prior to attaching the capture agent (e.g., the MAA protein adduct). Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the capture directly (in the cases of amino or thiol), or the activated surface can be further reacted with linkers such as glutaraldehyde, bis (succinimidyl) suberate, SPPD 9 succinimidyl 3-[2-pyridyldithio] propionate), SMCC (succinimidyl-4-[Nmaleimidomethyl] cyclohexane-1-carboxylate), SIAB (succinimidyl [4iodoacetyl] aminobenzoate), and SMPB (succinimidyl 4-[1maleimidophenyl] butyrate) to separate the capture agent from the surface. Vinyl groups can be oxidized to provide a means for covalent attachment. Vinyl groups can also be used as an anchor for the polymerization of various polymers such as poly-acrylic acid, which can provide multiple attachment points for specific capture agents Amino groups can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons; available from Sigma Chemical Co., St. Louis, Mo.). Additionally, poly-electrolyte interactions can be used to immobilize a MAA protein adduct on a solid phase using techniques and chemistries described U.S. Pat. Nos. 5,459,080, 5,459,078, and the like.

Other considerations affecting the choice of solid phase include the ability to minimize non-specific binding of labeled entities and compatibility with the labeling system employed. For, example, solid phases used with fluorescent labels should have sufficiently low background fluorescence to allow signal detection.

Following attachment of a specific capture agent, the surface of the solid support may be further treated with materials such as serum, proteins, or other blocking agents to minimize non-specific binding.

MAA Protein Adduct

In various embodiments an MAA protein adduct is used to capture/bind anti-MAA adduct antibodies that are present in the biological sample. Methods of making a MAA protein adduct are known to those of skill in the art and described, for example, in U.S. Pat. No. 5,939,535 and in Tuma et al. (1996) *Hepatology*, 23 (4): 872-880. Basically, acetaldehyde and malondialdehyde (MDA) react together in the presence of a protein (a substrate with an amino group) to form a distinct product comprising a hybrid adduct of MDA and acetaldehyde which has been designated malondialdehyde, acetaldehyde-adduct (MAA).

As described in U.S. Pat. No. 5,939,535, the adduct can readily be produced by treatment of the protein(s) of interest (e.g., albumin), e.g., at a concentration of 1 mg/ml with 1 mM acetaldehyde plus 1 mM MDA for 3 days at 37° C. Following overnight dialysis against 0.1 M phosphate buffer (pH 7.4 and 4° C.), the solution can be further handled as desired (e.g., adsorbed or covalently coupled to an ELISA well, microparticle, etc.).

However, depending on the type of macromolecule, concentrations of AA and MDA may need to be raised or lowered to achieve the same amount of fluorescents that makes MAA reactive.

The method of producing a MAA protein adduct is illustrative and non-limiting. Using the teachings provided herein, the MAA adducts can readily be produced using other methods.

Labeling Systems

Detectable labels suitable for use in the detection agents (e.g., antibodies that bind to anti-MAA adduct antibodies and form an anti-MAA adduct/anti-MAA adduct antibody complex) in the assays described herein include any composition detectable by spectroscopic, photochemical, biochemical, immunochemical, electrical, optical, or chemical means. Useful labels include, but are not limited to, magnetic beads (e.g., DYNABEADS®), fluorescent dyes (e.g., fluorescein, Texas Red, rhodamine, green fluorescent protein, and the like, see, e.g., Molecular Probes, Eugene, Oregon, USA), chemiluminescent compounds such as acridinium (e.g., acridinium-9-carboxamide), phenanthridinium, dioxetanes, luminol and the like, radiolabels (e.g., $^3$H, $^{125}$I, $^{35}$S, $^{14}$C, or $^{32}$P), catalysts such as enzymes (e.g., horse radish peroxidase, alkaline phosphatase, beta-galactosidase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The label can be attached to the detection agent prior to, or during, or after contact with the biological sample. So-called "direct labels" are detectable labels that are directly attached to or incorporated into detection agents (e.g., anti-IgG antibodies, anti-IgM antibodies, anti-IgA antibodies, etc.) prior to use in the assay. Direct labels can be attached to or incorporated into detection agents by any of a number of means well known to those of skill in the art.

In contrast, so-called "indirect labels" typically bind to the detection agent at some point during the assay. Often, the indirect label binds to a moiety that is attached to or incorporated into the detection agent prior to use. Thus, for example, an antibody used as a detection agent (a "detection antibody") can be biotinylated before use in an assay. During the assay, an avidin-conjugated fluorophore can bind the biotin-bearing detection agent, to provide a label that is easily detected.

In another example of indirect labeling, polypeptides capable of specifically binding immunoglobulin constant regions, such as polypeptide A or polypeptide G, can also be used as labels for detection antibodies. These polypeptides are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401-1406, and Akerstrom (1985) *J. Immunol.*, 135: 2589-2542). Such polypeptides can thus be labeled and added to the assay mixture, where they will bind to the detection antibody, as well as to the species-specific antibody, labeling both and providing a composite signal attributable to analyte and autoantibody present in the sample.

Some labels useful in methods described herein require the use of an indicator reagent to produce a detectable signal. In an ELISA, for example, an enzyme label (e.g., beta-galactosidase) may require the addition of a substrate (e.g., X-gal) to produce a detectable signal.

Illustrative Formats

Chemiluminescent Microparticle Immunoassay (CMIA)

In one illustrative embodiment a chemiluminescent label is employed in a chemiluminescent microparticle assay (CMIA) according to the invention. Generally, chemiluminescent microparticle assay techniques are based on the principle that a chemiluminescent label, when treated via a trigger reagent, will emit light at a characteristic wavelength (i.e., chemiluminescence).

The reactants necessary for CMIA can include microparticles coated with a capture agent specific for the analyte being measured, a chemiluminescent detection agent and a triggering agent (e.g., chemical or electrochemical). The reaction sequence for performing CMIA can include mixing the microparticles coated with a capture agent specific for the analyte with a sample in a reaction vessel to form an immune complex; washing the captured immune complex to remove unbound material; mixing the captured immune complex with a chemiluminescent detection agent; washing the captured immune complex-chemiluminescent detection agent; and mixing the captured immune complex-chemiluminescent detection agent with a triggering agent to initiate light emission.

Chemiluminophores useful in CMIA include acridinium (e.g., acridinium-9-carboxamide), luminol, dioxetane, ruthenium complexes and similar chemiluminescent derivatives. Microparticles useful in CMIA include diamagnetic, magnetic and paramagnetic microparticles. Examples of commercially available automated instruments with which chemiluminescent microparticle assay assays can be conducted include: Architect i-Systems and the Abbott Prism (all available from Abbott Laboratories, Abbott Park, Ill.).

Electrochemical Detection Systems

In other embodiments, immunoassays are carried out using electrochemical detection. A basic procedure for electrochemical detection has been described by Heineman and coworkers. This entailed immobilization of a primary antibody (Ab, rat-anti mouse IgG), followed by exposure to a sequence of solutions containing the antigen (Ag, mouse IgG), the secondary antibody conjugated to an enzyme label (AP-Ab, rat anti mouse IgG and alkaline phosphatase), and p-aminophenyl phosphate (PAPP). The AP converts PAPP to p-aminophenol (PAP$_R$, the "R" is intended to distinguish the reduced form from the oxidized form, PAP$_O$, the quinoneimine), which is electrochemically reversible at potentials that do not interfere with reduction of oxygen and water at pH 9.0, where AP exhibits optimum activity. PAP$_R$ does not cause electrode fouling, unlike phenol whose precursor, phenylphosphate, is often used as the enzyme substrate. Although PAP$_R$ undergoes air and light oxidation, these are easily prevented on small scales and short time frames. Picomole detection limits for PAP$_R$ and femtogram detection limits for IgG achieved in microelectrochemical immunoassays using PAPP volumes ranging from 20 μL to 360 μL have been reported previously. In capillary immunoassays with electrochemical detection, the lowest detection limit reported thus far is 3000 molecules of mouse IgG using a volume of 70 μL and a 30 min or 25 min assay time.

In one illustrative approach a test cartridge (similar to the Abbott Point of Care (i-STAT™) electrochemical immunoassay system) provides a MAA protein adduct on an electrochemical sensor fabricated in a silicon chip. Deposited in another location on the chip is an antibody/alkaline phosphatase conjugate (e.g., an anti-IgG conjugated to alkaline phosphatase). The biological sample (e.g., whole blood, plasma, etc.) is contacted with the sensor allowing the enzyme conjugate to dissolve into the sample. Anti-MAA adduct antibodies within the sample become labeled with the conjugate and this complex is captured onto the surface of the electrochemical sensor by binding of the anti-MAA adduct antibodies to the immobilized MAA adduct. The sample, as well as excess enzyme conjugate, is washed off the sensors. Within the wash fluid is a substrate for the alkaline phosphatase enzyme. The enzyme bound to the antibody/antigen/antibody sandwich cleaves the substrate releasing an electrochemically detectable product. The electrochemical (e.g., amperometric, voltammetric, etc.) sensor measures this enzyme product which is proportional to the concentration of anti-MAA adduct antibodies in the sample.

This electrochemical detection scheme is intended to be illustrative and not limiting. It is noted that other electrochemical detection methods are known to those of skill in the art and various electrochemical detection systems are described, for example, in U.S. Pat. Nos. 7,045,364, 7,045, 310, 6,887,714, 6,682,648, 6,670,115, and the like.

Lateral Flow Assays.

In certain embodiments the assays are formatted as lateral flow tests also known as lateral flow immunochromatographic assays. These assays are often produced in a test strip/dipstick format. In lateral flow assays the test sample flows along a solid substrate via capillary action. After the sample is applied to the test it encounters a colored reagent that mixes with the sample and transits the substrate encountering lines or zones that have been pretreated with (e.g., with antigen such as MAA adduct) and/or detection reagent (e.g., labeled antibody). Depending upon the analytes present in the sample the colored reagent can become bound at the test line or zone and can be quantified by comparison to a reference, or read electrochemically as described herein, or read optically using for example a reader. Lateral Flow Tests can operate as either competitive or sandwich assays.

Microfluidic Assays.

In certain embodiments the assays are performed using microfluidic devices. Microfluidic assays are well known to those of skill in the art. In one illustrative approach, fluorescent reactions of a heterogeneous sandwich enzyme-linked immunoassay (ELISA) in an all-PDMS [poly (dimethylsiloxane)] microfluidic device can be detected using a cooled charge coupled device (CCD) camera interfaced with an epifluorescence microscope. A PDMS chip microsensor has been successfully used to quantify a model analyte (sheep IgM) with sensitivity down to 17 nM. This hybrid integrated technique has been extended to on-chip imaging and quantification of light emission from a biochemical immunoassay in PDMS chip (see, e.g., Eteshola and Balberg (2004) *Biomedical Microdevices,* 6 (1): 7-9, and the like).

In certain embodiments evanescent biosensors are also contemplated. These biosensors do not require the pretreatment of a biological sample prior to detection of an analyte of interest. An evanescent biosensor generally relies upon light of a predetermined wavelength interacting with a fluorescent molecule, such as for example, a fluorescent label attached to a MAA adduct near the probe's surface, to emit fluorescence at a different wavelength upon binding of the analyte (e.g., anti-MAA adduct antibody).

It will be apparent to the skilled person that the assay formats described herein are amenable to any of a number of high throughput formats.

Biological Samples

In various embodiments the anti-MAA adduct IgG antibody measurements are made on biological samples derived from a subject of interest. Such subjects include, for example, a patient displaying one or more clinical symptoms, an asymptomatic patient undergoing routine examination, a patient displaying one or more cardiac risk factors (e.g., obesity, diabetes, smoker, family history of heart disease, etc.).

The sample is obtained using standard methods known to those of skill in the art, and in certain embodiments, ultimately standardized for a particular assay protocol. Typically, the biological sample will be one in which anti-MAA adduct antibodies are expected to be found if they are present at all in the subject. Such samples include, but are not limited to saliva/sputum, blood or blood fractions (e.g., plasma, serum), certain tissue biopsies, and the like.

In one embodiment a biological sample is obtained from a subject by a method selected from the group consisting of surgery or other excision method, aspiration of a body fluid such as hypertonic saline or propylene glycol, broncheoalveolar lavage, bronchoscopy, saliva collection with a glass tube, salivette (Sarstedt A G, Sevelen, Switzerland), Orasure (Epitope Technologies Pty Ltd, Melbourne, Victoria, Australia), omni-sal (Saliva Diagnostic Systems, Brooklyn, N.Y., USA) and blood collection using any method known in the art, such as, for example using a syringe.

In various embodiments the sample may be treated to facilitate storage and/or processing in the assay, and/or standardization of the assay.

EXAMPLES

The following examples are offered to illustrate, but not to limit the claimed invention.

Example 1

Anti-MAA Immunoglobulin Isotypes in Inflammatory Bowel Disease: Novel Diagnostic Implications for Ulcerative Colitis Inflammatory bowel disease (IBD) is a conglomerate of chronic inflammatory disorders of the gut where ulcerative colitis (UC) and Crohn's Disease (CD) are the principal manifestations. The etiology of IBD is uncertain and its proper diagnosis requires a multitude of invasive diagnostic procedures. Beyond being invasive, these diagnostic measures are expensive, uncomfortable and sometimes life threatening. Moreover, due to the potential crossover of the pathobiology and symptoms, clear diagnosis of the UC versus CD is difficult, especially during initial diagnosis. Clearly, an urgent need for noninvasive and reliable diagnostic biomarkers exist. This study aimed at developing a noninvasive serum based diagnostic biomarker, that can differentiate IBD patients with high confidence.

Malondialdehyde (MDA), a lipid peroxidation product, is a naturally occurring highly reactive compond implicated in promoting autoimmunity and inflammation. MDA breaks down to form acetaldehyde (AA), which combines with MDA to form a unique MDA-AA adduct (MAA). MAA is highly stable and induces immunogenic reactions even in the absence of adjuvant, and result in adaptive immune responses to the carrier protein itself, thus bypassing tolerance. Considering the recent reports that increased MAA levels correlates with certain autoimmune pathobiology, we wondered if MAA-antibody can also serve as non-invasive biomarker for the IBD.

To test our hypothesis, we investigated the level of MAA antibodies in the serum and plasma, and modified protein in tissues samples from a murine model of colitis. Further validation was done by examining MAA antibody isotypes in the IBD patient serum samples by ELISA.

Our initial data using serum and colon tissue samples from murine model of DSS-colitis demonstrated a significant increase in anti-MAA antibody reactivity in colitis versus control mice (p<0.0001). In subsequent analysis, we utilized serum samples from 107 IBD patients [(79 with UC, 20 with CD, 8 samples from lymphocytic colitis (LC)] and 24 healthy controls. Serum levels of immunoglobulin-(Ig)-G, Ig-M, and Ig-A) anti-MAA isotypes were screened (see, FIG. 1. Remarkably, Ig M levels were significantly higher in the LC (p<0.0001 versus normal, UC or CD) but not significantly different between the normal, CD and UC patients (see, FIG. 1, panel C). In contrast, Ig G levels were significantly higher in the UC patients (p<0.001 versus normal, CD or LC) (see, FIG. 1, panel A) however not significantly different between the normal, CD and LC patients. Similar was the case for the Ig~A (p<0.001) reactivity (see, FIG. 1, panel A). Taken together, our data revealed novel abilities of the MAA~IgG and IgA antibody levels to differentiate the UC patients with high confidence suggesting that these specific isotypes of anti-MAA immunoglobulin can serve as promising serological diagnostic biomarker not only for the diagnosis of UC patients but also to differentiate them from CD or LC patients. Further analysis to determine if these isotypes can also predict disease severity and therapy response are currently underway.

Example 2

Serum Anti-MAA Antibodies Increase in Inflammatory Bowel Disease and Separate Ulcerative Colitis from Crohn's Disease

Summary of Example 2

Inflammatory bowel disease (IBD) comprises of ulcerative colitis (UC) and Crohn's Disease (CD). Precise molecular pathogenesis of IBD is unclear; however, role of oxidative stress in promoting IBD is widely recognized. Malondialdehyde (MDA), a lipid peroxidation product highly elevated in IBD, reacts with acetaldehyde and forms a unique Malondialdehyde-Acetaldehyde Adduct (MAA). However, the role of MAA-modification and/or anti-MAA antibodies in IBD has not been examined. This study was undertaken to address this knowledge gap.

We collected data from 171 IBD (UC-103 and CD-68) patients and 43 healthy controls (HC) from two independent cohorts. ELISA was done to determine the blood levels of Ig-G, Ig-M and Ig-A anti-MAA isotypes. Receiver Operating Characteristic (ROC) curves were performed to evaluate the Anti-MAA antibodies discriminatory capacity. Univariate and multivariate logistic regression helped compare different groups. The Youden cut-off index from the ROC curve was used to determine the biomarker test's sensitivity and specificity.

The blood anti-MAA antibody levels were significantly elevated in IBD patients. Also, serum Ig-G anti-MAA antibody level was significantly (p<0.0001) higher in UC compared to the CD patients. Anti-MAA Ig-G levels also differentiated UC patients from CD patients with only colon involvement (<0.01). Logistic regression and ROC curves analysis revealed that the Ig-G anti-MAA level could accurately differentiate UC from CD. Combining the Ig-G anti-MAA levels with inflammatory markers interleukin (IL)-1β and IL-6 further augmented the power to discriminate UC from CD.

We demonstrate that serum Ig-G anti-MAA antibody levels can serve as a novel, non-invasive and highly sensitive biomarker for differentiating UC from CD.

Materials and Methods

Study Design and Patients Recruitment:

This was a cross-sectional study performed at the University of Nebraska Medical Center, Omaha, NE using two independent patient cohorts. The Nebraska cohort (adult cohort) consisted of primarily adult IBD patients who were attended at the University of Nebraska Medical Center, Omaha, NE The Cincinnati cohort (pediatric cohort) consisted of younger IBD patients enrolled prospectively at Cincinnati Children's Hospital Medical Center, Cincinnati, Ohio. Descriptive data were collected from the patients in both cohorts however patient records were de-identified. The descriptive data and comparisons of above two cohorts by diagnostic groups are shown in Table 2. The study was approved by the Institutional Review Board at both locations.

healthy controls as described previously and briefly explained in the supplementary methods.[5]

Statistical Analysis:

Patient characteristics and biomarkers were analyzed by diagnosis using the Kruskal-Wallis test, and Wilcoxon test for pairwise comparisons for the comparison between groups. Adjustments for multiple comparisons were made using Bonferroni's method. Mean values with standard deviation were used for independent student t-tests or one-way ANOVA, and corrections for multiple comparisons were made using Tukey's multiple comparison tests in Prism 9.0 (GraphPad Software, Inc.). A P-value<0.05 was defined as statistically significant. Multivariate logistic regression and ROC curves were used to examine the markers and potential combinations as predictors of specific disease while adjusting for age as a continuous variable. ROC curves were used to determine optimal marker cut points in

TABLE 2

Descriptive characteristics of the IBD patient cohorts.

Cohort 1 (Adult Cohort)

| | | UC (n = 81) | CD (n = 21) | HC (n = 25) | p-value |
|---|---|---|---|---|---|
| Age | Median (IQR) | 52.4 (37.6-64.4) | 66.0 (56.0-72.0) | 44.0 (36.1-59.4) | 0.0058 |
| Gender | Female | 33 (41%) | 12 (57%) | 12 (48%) | 0.38 |
| | Male | 48 (59%) | 9 (43%) | 13 (52%) | |
| Race/ethnicity | Black | 3 (4%) | 1 (5%) | 8 (32%) | <0.001 |
| | Hispanic | 1 (1%) | 0 | 3 (12%) | |
| | Other | 1 (1%) | 0 | 1 (4%) | |
| | White | 76 (94%) | 20 (95%) | 13 (52%) | |

Cohort-2 (Pediatric Cohort)

| | | UC (n = 22) | CD (n = 47) | HC (n = 18) | p-value |
|---|---|---|---|---|---|
| Age | Median (Range) | 16.4 (7.7-21.3) | 15.7 (5.6-21.7) | 16.30 (9.0-18.0) | 0.41 |
| Gender | Female | 14 (64%) | 16 (34%) | 10 (56%) | 0.047 |
| | Male | 8 (36%) | 31 (66%) | 8 (44%) | |
| Race/ethnicity | Black | 1 (5%) | 3 (6%) | 3 (17%) | 0.55 |
| | Hispanic | 1 (5%) | 1 (2%) | 0 | |
| | White | 20 (90%) | 44 (91%) | 15 (83%) | |
| Disease site | Colonic | — | 16 (34%) | — | |
| | Ileal (L1) | | 5 (11%) | | |
| | Ileocolonic (L3) | | 26 (55%) | | |
| Perianal Involvement, Fistula | No | — | 31 (65%) | — | |
| | Yes | | 16 (34%) | | |
| Crohn's disease behavior | Non-stricturing, non-penetrating | — | 38 (83%) | — | |
| | Penetrating | | 3 (7%) | | |
| | Stricturing | | 5 (11%) | | |
| Colitis Classification | Extensive | 3 (14%) | — | — | |
| | Left-sided | 3 (14%) | | | |
| | Pancolitis | 14 (64%) | | | |
| | Proctitis | 2 (9%) | | | |
| Oral 5 - ASA | Yes | 16 (73%) | 7 (15%) | — | <0.001 |
| Oral Steroids | Yes | 8 (36%) | 8 (17%) | — | 0.12 |
| Rectal Steroids | Yes | 2 (9%) | 2 (4%) | — | 0.58 |
| 6 - MP or Azathioprine | Yes | 3 (14%) | 13 (28%) | — | 0.23 |
| Methotrexate | Yes | 1 (5%) | 2 (4%) | — | 1.0 |
| Antibiotic | Yes | 0 | 6 (13%) | — | 0.17 |
| Anti-TNF Biologic | Yes | 5 (22%) | 13 (28%) | — | 0.77 |
| Anti-Leukocyte Trafficking Biologic | Yes | 0 | 2 (4%) | — | 1.0 |

Circulating Serum Anti-MAA Immunoglobulin Detection:

A direct (coated antigen) Enzyme-linked immunosorbent assay (ELISA) was used to determine the levels of anti-MAA Immunoglobulins in the serum from UC, CD, and prediction based on the model. To find an optimal combination of biomarkers for predicting UC, CD, and healthy, recursive partitioning methods were used in a classification model[11]. The portioning trees were created using the "party"

package: A Laboratory for Recursive Partitioning in the R version 3.2.0 programming language.[12,13]

Results

Demographic Characteristics of the Patient Cohorts:

In this study, we used blood (serum/plasma) samples from 171 IBD patients and 43 controls from two independent cohorts and biopsy samples (n #3/group). The Nebraska cohort was termed "adult cohort" and consisted of 127 adult participants, which included 102 IBD (81 UC and 21 CD) patients and 25 healthy controls (HC). Descriptive characteristics of the patients and HC are shown in Table 2. The differences between patient ages in this cohort were adjusted in relevant analyses. The second cohort involved younger (children) individuals and was named as "pediatric cohort". This cohort was comprised of 69 IBD patients (22 UC and 47 CD) and 18 HC samples (Table 2).

Figure 2:
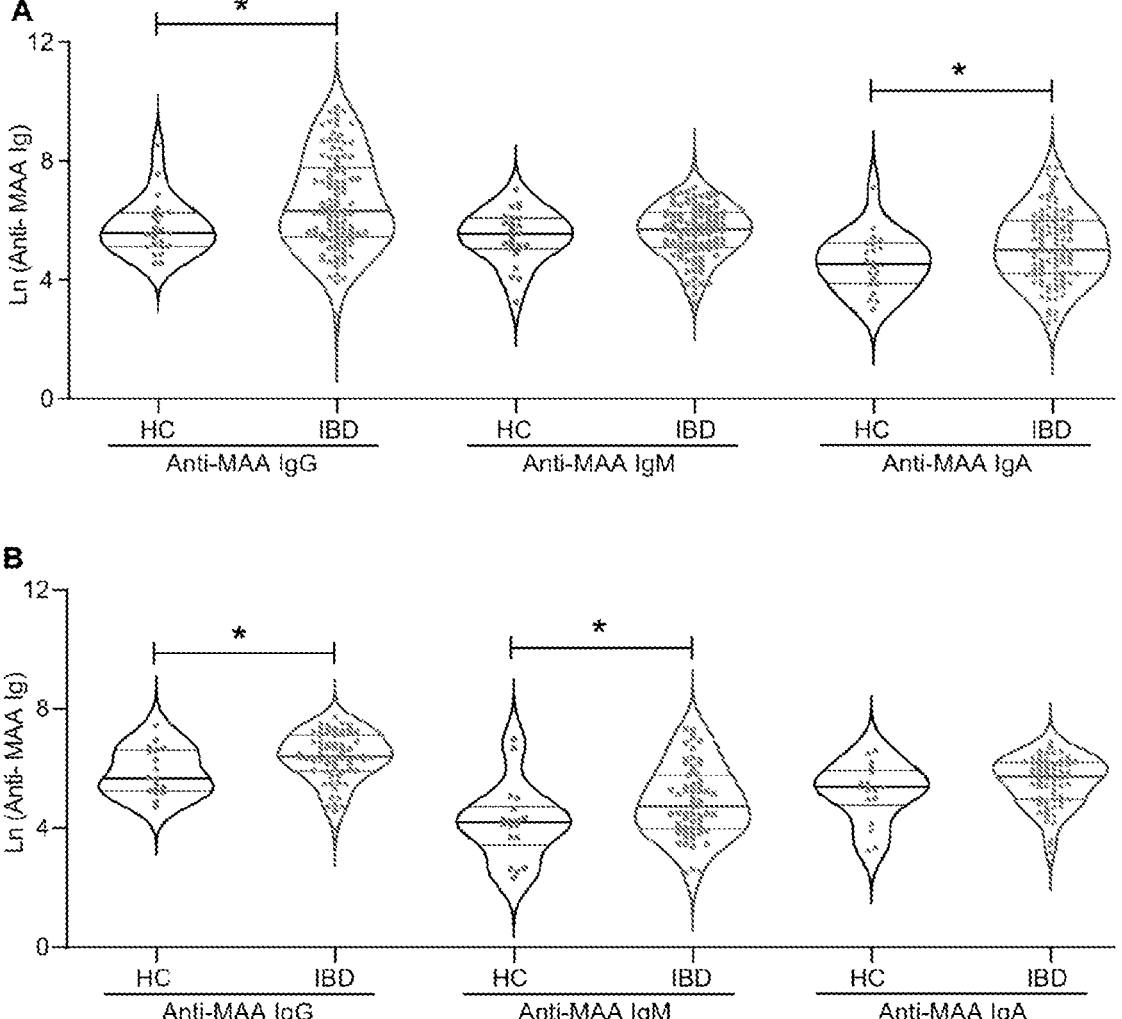
FIG. 2, panels A-B, shows that differential levels of anti-MAA immunoglobulins isotypes were detected in IBD. ELISA immunoassay was used to measure the blood level of anti-MAA immunoglobulins isotypes. Data were transformed into natural log scale and violin plots were used to demonstrate the differences among the groups. Panel A) Serum level of anti-MAA antibodies in Nebraska/adult cohort. Panel B) Plasma level of anti-MAA immunoglobulins in Cincinnati/pediatric cohort. *p<0.05.

Serum Anti-MAA IgG Level Increases in IBD Patients:

Considering that the MAA-adducts and antibodies to MAA increase in certain autoimmune inflammatory diseases[1], we examined the status of anti-MAA immunoglobulin isotypes in the serum of the Nebraska/adult cohort. As shown in FIG. 2, panel A, the Ig-G and IgA anti-MAA antibody levels were significantly upregulated in IBD patients (versus HC; P<0.05). The levels of IgM anti-MAA antibodies did not differ between the groups under consideration (FIG. 2, panel A). To validate these findings, we used an independent IBD patient cohort from a different institute (Cincinnati cohort). Interestingly, in Cincinnati cohort consisting of younger individuals, we found that the IgM and not IgA anti-MAA antibody levels were significantly different. Irrespective, we found significant IgG anti-MAA antibody levels compared to HC, similar to the Nebraska cohort (P<0.05; 2, panel B). Overall, data from both cohorts revealed a consistent upregulation in blood IgG anti-MAA immunoglobulins in IBD patients compared to HC.

Increased Blood Level of Anti-MAA IgG in IBD is Specific to UC:

IBD is a conglomerate of chronic inflammatory disorders of the gut where UC and CD are the principal but diverse subtypes[14]. Based on differing pathobiology of UC and CD, we further investigated whether the increase in serum IgG anti-MAA levels are specific for one subtype or are similar in both of these diseases. To assess the specificity of anti-MAA antibodies in classifying IBD patients into subtype, adjusted multiple comparison analysis was done as shown in Table 3. Serum ELISA levels of anti-MAA antibodies were significantly different between the diagnostic groups (UC vs. CD and UC vs. HC; IgG P<0.0001; IgA P<0.05). This analysis also suggested that IgG anti-MAA levels are significantly increased in UC patients compared to HC (FIG. 3, panel A; P<0.01). In contrast, no significant differences were found in IgM and IgA levels in UC compared to CD (FIG. 2, panels A-B and Table 3).

TABLE 3

| Serum immunoglobulins isotypes comparisons by diagnosis groups in both cohorts | | | | |
|---|---|---|---|---|
| Label | p-value | UC vs CD | UC vs HC | CD vs HC |
| Adult Cohort | | | | |
| Anti MAA IgG | Unadjusted | <0.0001 | 0.0005 | 0.23 |
| | Adjusted* | <0.0001 | 0.0006 | 0.70 |

TABLE 3-continued

| Serum immunoglobulins isotypes comparisons by diagnosis groups in both cohorts | | | | |
|---|---|---|---|---|
| Label | p-value | UC vs CD | UC vs HC | CD vs HC |
| Anti MAA IgA | Unadjusted | 0.16 | 0.017 | 0.75 |
| | Adjusted | 0.49 | 0.052 | 1.0 |
| Pediatric Cohort | | | | |
| Anti MAA IgG | Unadjusted | <0.0001 | <0.0001 | 0.32 |
| | Adjusted* | <0.0001 | <0.0001 | 0.97 |
| Anti MAA IgM | Unadjusted | 0.0229 | 0.0012 | 0.31 |
| | Adjusted* | 0.069 | 0.0036 | 0.94 |
| Anti MAA IgA | Unadjusted | 0.0575 | 0.027 | 0.46 |
| | Adjusted | 0.17 | 0.081 | 1.0 |

*p-values adjusted for multiple comparisons with Bonferroni method

Figure 3:
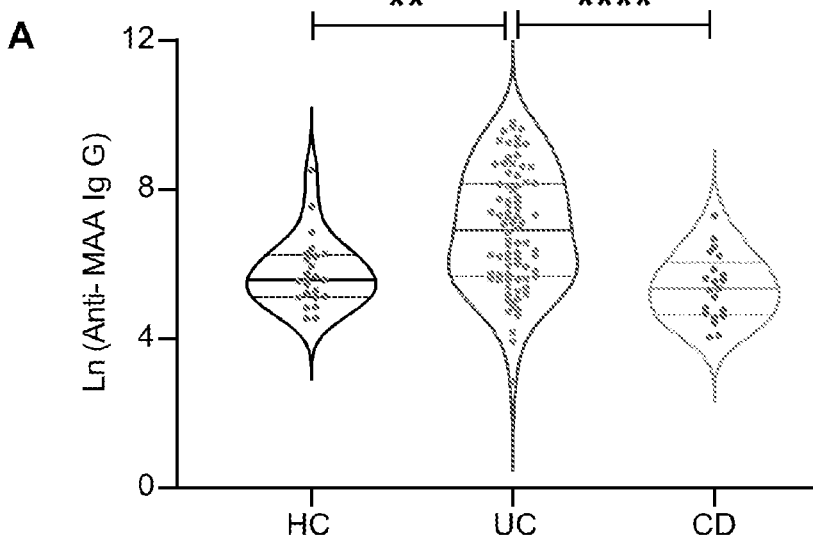
FIG. 3, panels A-B, shows that IgG anti-MAA immunoglobulin precisely separate UC from CD. Panels A-B) Comparative serum/plasma IgG anti-MAA antibody analysis in both Nebraska/adult (panel A) and Cincinnati/pediatric cohorts (panel B). Values are presented as natural log transformed scale. *p<0.05 and ****p<0.0001
Figure 3:
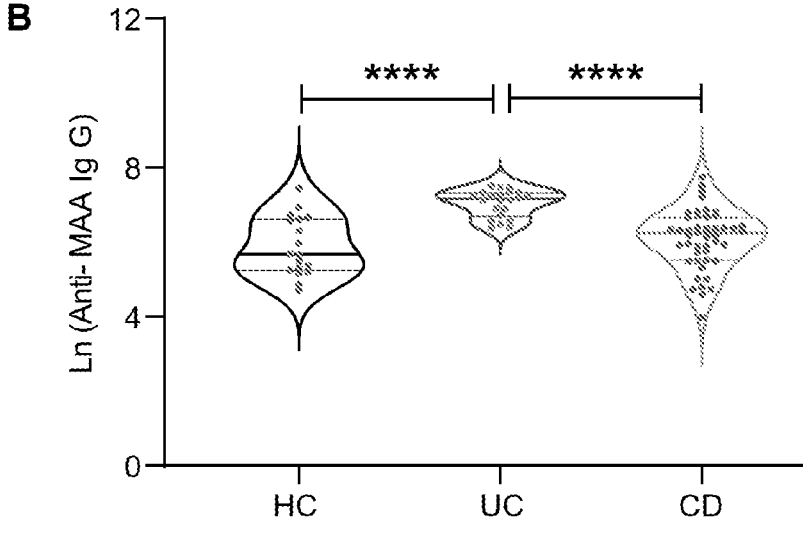
Figure 8:
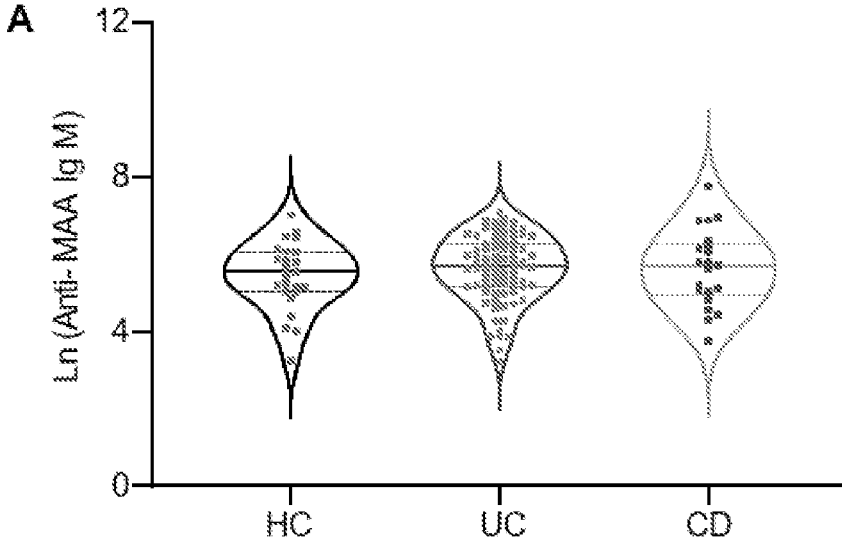
FIG. 8, panels A-D, shows a comparison of serum levels of anti-MAA immunoglobulins isotypes in the IBD. Serum level of anti-MAA IgM and IgA are shown in Nebraska/adult cohort (panels A-B), and Cincinnati/Pediatric cohorts (panels C-D). Data were transformed into natural log scale. *p>0.05
Figure 8:
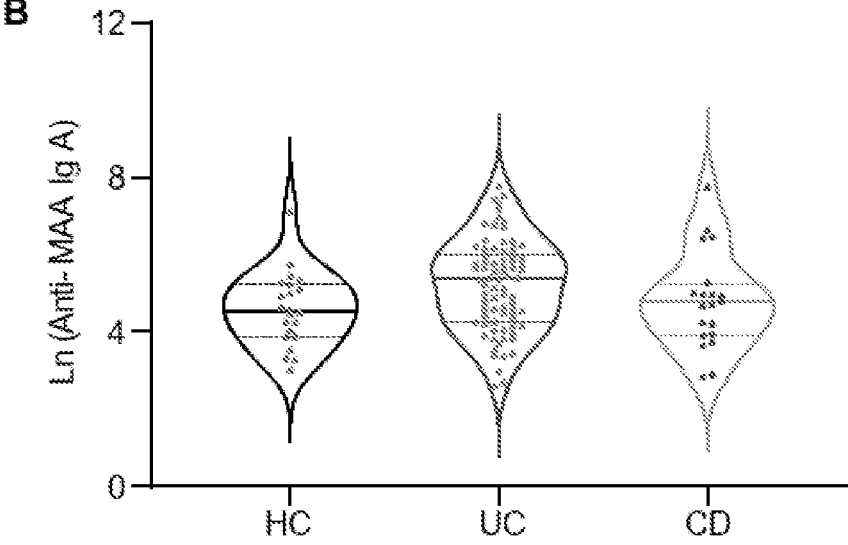

Remarkably, similar to the Nebraska cohort, only IgG anti-MAA antibody levels were significantly increased when comparing UC patients with HC and CD patients in the Cincinnati cohort (FIG. 3, panel B; P<0.0001). Adjusted multiple comparisons revealed that IgG anti-MAA was significantly different in UC vs. CD, P<0.0001, and UC vs. HC, P<0.0001. In contrast, IgM anti-MAA was found to be significantly different only in UC vs HC (P<0.05) (FIG. 8, panels C-D and Table 3). Overall, the data from both adult and children cohorts revealed that an increase in serum IgG anti-MAA is the specific for UC and may be useful diagnostically.

Figure 4:
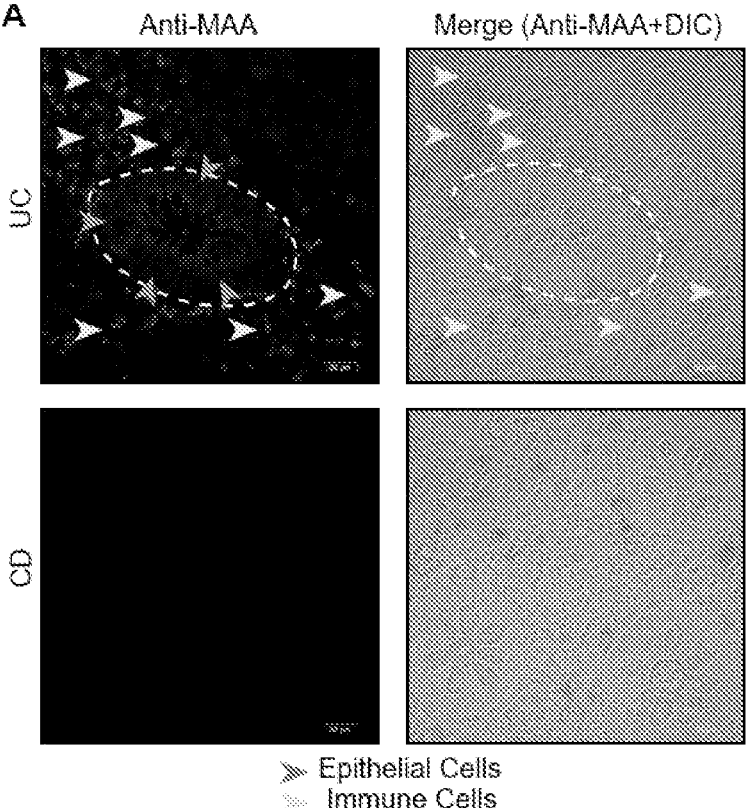
FIG. 4, panels A-B, shows that MAA adduct is increased in IBD patients. Confocal immunofluorescence analysis of MAA was done in the biopsy samples from UC and CD patients (n #3). Representative images (panel A) and quantitative analysis of the signal intensity (panel B) of MAA adduct are shown. Values are presented as mean+SEM. ***P<0.001
Figure 4:
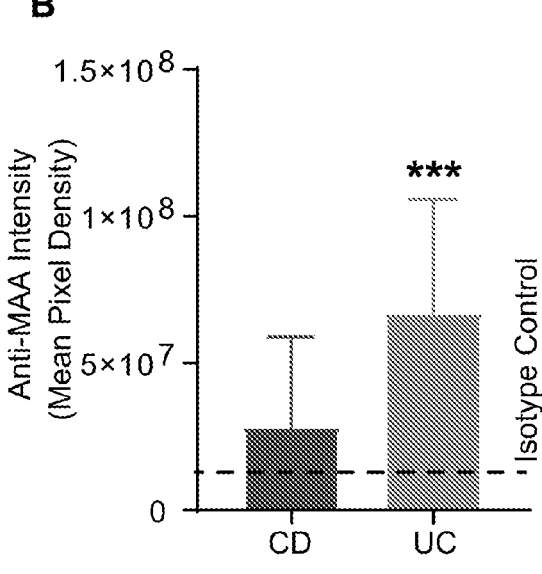

MAA-Adducts Formation is Robustly Upregulated in UC:

Having uncovered a novel finding of specific increase in serum levels of anti-MAA IgG in UC patients, we considered the significance of MAA adduct in the face of the immunogenic potential that triggers anti-MAA IgG production. We postulated an increased level of MAA-adducts in UC patients. To test, we visualized the presence of MAA adduct in both, CD and UC patient biopsies using immunofluorescence. As shown in FIG. 4, panel A, biopsy sections from the UC patients reacted stronger to the anti-MAA antibody (blue color) in both epithelial and immune cells. Staining intensity analysis confirmed that the mean pixel density of the antibody reactivity increases significantly in the UC compared to the CD (FIG. 4, panel B; P<0.001). In summary, increased MAA-adducts reflected excessive lipid peroxidation in IBD and precisely discriminated UC patients from CD patients.

Correlation Between Anti-MAA Ig Isotypes and Inflammatory Cytokines:

We have found altered level anti-MAA antibodies in IBD samples (FIG. 2, panels A-B, Table 3). Additionally, we estimated the serum levels IL-1β and IL-6 that play important role in IBD patho-biology and disease progression (Table 4).[15] We then assessed the correlation coefficient between serological levels of anti-MAA antibodies and these inflammatory cytokines.

TABLE 4

| Serum level of IL-1β and IL-6 is altered in both cohorts. | | | | | | | | |
| --- | --- | --- | --- | --- | --- | --- | --- | --- |
| Adult Cohort | | | | | | | | |
| Variable | | N | Mean | SD | Median | Minimum | Maximum | Overall p-value |
| IL-1p | UC | 81 | 0.51 | 1.12 | 0.20 | 0.01 | 7.37 | 0.070 |
| | CD | 21 | 0.27 | 0.39 | 0.13 | 0.01 | 1.36 | |
| | HC | 25 | 0.56 | 0.65 | 0.23 | 0.02 | 2.19 | |
| IL-6 | UC | 81 | 15.46 | 65.39 | 3.60 | 0.39 | 572.34 | 0.47 |
| | CD | 21 | 12.32 | 17.72 | 5.22 | 0.44 | 70.52 | |
| | HC | 25 | 10.52 | 17.50 | 4.06 | 0.07 | 78.48 | |

| Label | p-value | UC vs CD | UC vs HD | CD vs HC |
| --- | --- | --- | --- | --- |
| IL-1β | Unadjusted | 0.34 | 0.081 | 0.019 |
| | Adjusted | 1.0 | 0.24 | 0.058 |

| Pediatric Cohort | | | | | | | | |
| --- | --- | --- | --- | --- | --- | --- | --- | --- |
| Variable | | N | Mean | SD | Median | Minimum | Maximum | Overall p-value |
| IL-1p | UC | 22 | 0.09 | 0.14 | 0.04 | 0.01 | 0.59 | 0.11 |
| | CD | 46 | 0.71 | 3.65 | 0.13 | 0.01 | 24.86 | |
| | HC | 18 | 0.15 | 0.17 | 0.08 | 0.00 | 0.55 | |
| IL-6 | UC | 22 | 1.30 | 0.79 | 1.04 | 0.33 | 3.70 | 0.30 |
| | CD | 46 | 1.96 | 1.85 | 1.25 | 0.13 | 7.46 | |
| | HC | 18 | 1.25 | 1.19 | 0.80 | 0.14 | 4.54 | |

In Tables 5 and 6, among the groups, correlation analyses indicated the significant associations among the serum level of anti-MAA Ig isotypes in both cohorts. However, as shown in Table 5 and Table 6, we do not find any significant correlation between serum level of cytokines and anti-MAA Ig isotypes.

TABLE 5

| Correlations of serum anti-MAA immunoglobulins, IL-1β and IL-6 among diagnostic group in adult cohort. | | | | | |
| --- | --- | --- | --- | --- | --- |
| | log IgG | log IgM | log IgA | log LL-1β | log IL-6 |
| Log IgG | 1.00000 | 0.23309 | 0.49800 | −0.12060 | 0.08045 |
| ln (Anti MAA IgG) | 126 | 0.0095 | <0.0001 | 0.1786 | 0.3705 |
| | | 123 | 120 | 126 | 126 |
| Log IgM | 0.23309 | 1.00000 | 0.31853 | −0.03589 | 0.05815 |
| Ln (Anti MAA IgM) | 0.0095 | 124 | 0.0004 | 0.6923 | 0.5212 |
| | 123 | | 118 | 124 | 124 |
| Log IgA | 0.49800 | 0.31853 | 1.00000 | 0.02152 | 0.09804 |
| ln(Anti MAA IgA) | <.0001 | 0.0004 | 121 | 0.8148 | 0.2847 |
| | 120 | 118 | | 121 | 121 |
| Log IL-1β | −0.12060 | −0.03589 | 0.02152 | 1.00000 | 0.37800 |
| | 0.1786 | 0.6923 | 0.8148 | 127 | <0.0001 |
| | 126 | 124 | 121 | | 127 |
| Log IL-6 | 0.08045 | 0.05815 | 0.09804 | 0.37800 | 1.00000 |
| | 0.3705 | 0.5212 | 0.2847 | <.0001 | 127 |
| | 126 | 124 | 121 | 127 | |

TABLE 6

| The correlations of serum anti-MAA immunoglobulins between the diagnostic groups and serum level of IL-1β and IL-6. | | | | | |
| --- | --- | --- | --- | --- | --- |
| | Log IgG | Log IgM | Log IgA | logIL-1p | logIL-6 |
| Log IgG | 1.00000 | 0.16819 | 0.19407 | 0.04069 | −0.15389 |
| ln(Anti MAA IgG) | 87 | 0.1384 | 0.0769 | 0.7099 | 0.1572 |
| | | 79 | 84 | 86 | 86 |
| Log IgM | 0.16819 | 1.00000 | 0.42147 | 0.12613 | 0.25098 |
| ln(Anti MAA IgM) | 0.1384 | 79 | 0.0001 | 0.2712 | 0.0267 |
| | 79 | | 77 | 78 | 78 |

TABLE 6-continued

The correlations of serum anti-MAA immunoglobulins between
the diagnostic groups and serum level of IL-1β and IL-6.

| | Log IgG | Log IgM | Log IgA | logIL-1p | logIL-6 |
|---|---|---|---|---|---|
| Log IgA | 0.19407 | 0.42147 | 1.00000 | −0.06363 | 0.34340 |
| ln(Anti MAA IgA) | 0.0769 | 0.0001 | 84 | 0.5677 | 0.0015 |
| | 84 | 77 | | 83 | 83 |
| Log IL-1β | 0.04069 | 0.12613 | −0.06363 | 1.00000 | 0.12644 |
| | 0.7099 | 0.2712 | 0.5677 | 86 | 0.2460 |
| | 86 | 78 | 83 | | 86 |
| Log IL-6 | −0.15389 | 0.25098 | 0.34340 | 0.12644 | 1.00000 |
| | 0.1572 | 0.0267 | 0.0015 | 0.2460 | 86 |
| | 86 | 78 | 83 | 86 | |

Anti-MAA IgG Level Reflects Disease Heterogeneity and is Independent of Disease Location in IBD:

Our data (FIG. 3, panels A-B) showed increase in serum level of anti-MAA IgG in UC, which is localized to the colon. The CD can affect any portion of the gut tract from the mouth to the anus. However, in approximately 15-20% of CD patients where disease is localized to colon; it is a critical confounding factor in the differential diagnosis in IBD.[16] To examine if observed increase in anti-MAA IgG antibody is specific to UC or limited to colon only, we further analyzed the plasma level of anti-MAA IgG antibodies among HC, UC, and colonic CD patients. Interestingly, the anti-MAA IgG level was significantly higher in UC even compared to the CD with colonic involvement (FIG. 5, panel A; $p<0.01$; UC vs HC-$p<0.0001$). Overall, these results indicate that increased serum anti-MAA IgG level in IBD is novel, location independent and specific to UC patients.

Serum Anti-MAA IgG is Strongly Associated With UC:

We have found increased levels of both, MAA-adducts and anti-MAA antibodies in UC patients compared to the CD patients. Therefore, we examined the association potential of immunoglobulin isotypes in the diagnosis of UC from CD and performed binary logistic regression analysis. Results from the adult cohort suggested a significant association of IgG anti-MAA isotype with UC [OR=2.38 (95% CI: 1.47-3.839); p=0.0004) and with addition of IL-1β and IL-6 [OR=2.67 (95% CI: 1.61-4.43); p=0.0002] from those with CD (Table 7). Interestingly, the outcome from Pediatric cohort showed even stronger association with increased odds ratio [OR=17.42 (95% CI: 4.2-70.78); p<0.0001) and with addition of inflammatory marker IL-1β and IL-6 [OR=30.95 (95% CI: 5.26-182.10); p=0.0001] (Table 8). Overall, serum anti-MAA IgG is firmly associated with UC.

TABLE 7

Logistic regression analysis revealed that serum IgG anti-MAA level significantly differentiate
the IBD patients from the healthy control and UC from CD in adults cohort,

| | OR | Lower CI | Upper CI | p-value | AUC | Lower CI | Upper CI | Cutpoint* | Sensitivity | Specificity |
|---|---|---|---|---|---|---|---|---|---|---|
| Ln IgG | 2.375 | 1.474 | 3.828 | 0.0004 | 0.8072 | 0.7121 | 0.9024 | Ln(IgG) > 5.711 IgG > 166.9 | 0.753 | 0.714 |
| Ln IgM | 0.969 | 0.555 | 1.691 | 0.91 | 0.4951 | 0.3406 | 0.6497 | Ln(IgM) < 6.86 IgM < 953.6 | 0.974 | 0.190 |
| Ln IgA | 1.333 | 0.870 | 2.043 | 0.19 | 0.6019 | 0.4568 | 0.7470 | Ln(IgA) > 5.37 IgA > 214.5 | 0.506 | 0.800 |
| Ln IL-1β | 1.141 | 0.860 | 1.514 | 0.36 | 0.5685 | 0.4322 | 0.7047 | Ln(IL-1β) > −1.764 IL-1β > 0.173 | 0.568 | 0.667 |
| Ln IL-6 | 0.829 | 0.582 | 1.181 | 0.30 | 0.5920 | 0.4511 | 0.7329 | Ln(IL-6) < 1.316 IL-6 < 3.729 | 0.519 | 0.714 |
| Ln IgG | 2.694 | 1.514 | 4.792 | 0.0007 | 0.7949 | 0.6949 | 0.8949 | Pr(UC) > 0.855 | 0.557 | 0.950 |
| ln IgA | 0.748 | 0.432 | 1.296 | 0.30 | | | | | | |
| Ln IgG | 2.827 | 1.635 | 4.888 | 0.0002 | 0.8156 | 0.7246 | 0.9067 | Pr(UC) > 0.823 | 0.641 | 0.905 |
| ln IgM | 0.641 | 0.350 | 1.175 | 0.15 | | | | | | |
| Ln IgG | 2.633 | 1.558 | 4.449 | 0.0003 | 0.8089 | 0.7153 | 0.9026 | Pr(UC) > 0.748 | 0.741 | 0.810 |
| ln IL-1β | 1.330 | 0.950 | 1.863 | 0.097 | | | | | | |
| Ln IgG | 2.379 | 1.487 | 3.808 | 0.0003 | 0.8172 | 0.7265 | 0.90 | Pr(UC) > 0.753 | 0.790 | 0.762 |
| Ln IL-6 | 0.771 | 0.511 | 1.164 | 0.22 | | | | | | |
| Ln IgG | 2.668 | 1.606 | 4.433 | 0.0002 | 0.8419 | 0.7515 | 0.9322 | Pr(UC) > 0.799 | 0.753 | 0.857 |
| ln IL-1β | 1.583 | 1.048 | 2.391 | 0.029 | | | | | | |
| ln IL-6 | 0.602 | 0.362 | 1.002 | 0.051 | | | | | | |

TABLE 8

Logistic regression analysis of serum anti-MAA IgG discriminate
UC patients from CD and healthy individuals in pediatric cohort.

| | OR | Lower CI | Upper CI | p-value | AUC | Lower CI | Upper CI | Cutpoint* | Sensitivity | Specificity |
|---|---|---|---|---|---|---|---|---|---|---|
| Ln IgG | 17.242 | 4.200 | 70.779 | <0.0001 | 0.8801 | 0.7988 | 0.9614 | Ln(IgG) > 6.406<br>IgG > 605.8 | 0.955 | 0.723 |
| Ln IgM | 1.563 | 0.983 | 2.485 | 0.059 | 0.6772 | 0.5424 | 0.8119 | Ln(IgM) > 4.333<br>IgM < 76.1 | 0.909 | 0.487 |
| Ln IgA | 2.281 | 1.040 | 5.001 | 0.040 | 0.6466 | 0.5121 | 0.7810 | Ln(IgA) > 5.171<br>IgA > 176.1 | 0.905 | 0.400 |
| Ln IL-1$\beta$ | 0.675 | 0.467 | 0.977 | 0.037 | 0.6537 | 0.5145 | 0.7928 | Ln(IL1$\beta$) < −2.367<br>IL1$\beta$ < 0.094 | 0.773 | 0.587 |
| Ln IL-6 | 0.846 | 0.472 | 1.516 | 0.57 | 0.5494 | 0.4126 | 0.6862 | Ln(IL-6) < 0.664<br>IL-6 < 1.943 | 0.909 | 0.413 |
| Ln IgG<br>In IgA | 18.332<br>2.996 | 3.908<br>0.953 | 85.995<br>9.421 | 0.0002<br>0.061 | 0.8921 | 0.8154 | 0.9688 | Pr(UC) > 0.260 | 0.952 | 0.756 |
| Ln IgG<br>In IgM | 27.573<br>2.252 | 4.645<br>1.080 | 163.69<br>4.698 | 0.0003<br>0.030 | 0.9021 | 0.8177 | 0.9865 | Pr(UC) > 0.471 | 0.909 | 0.872 |
| Ln IgG<br>In IL-1$\beta$ | 20.775<br>0.566 | 4.487<br>0.341 | 96.197<br>0.939 | 0.0001<br>0.028 | 0.8982 | 0.8209 | 0.9755 | Pr(UC) > 0.486 | 0.818 | 0.891 |
| Ln IgG<br>Ln IL-6 | 21.298<br>1.518 | 4.509<br>0.693 | 100.592<br>3.326 | 0.0001<br>0.30 | 0.8834 | 0.8038 | 0.9630 | Pr(UC) > 0.249 | 0.909 | 0.761 |
| Ln IgG<br>In IL-1$\beta$<br>In IL-6 | 30.946<br>0.535<br>1.833 | 5.259<br>0.317<br>0.771 | 182.097<br>0.903<br>4.360 | 0.0001<br>0.019<br>0.17 | 0.9061 | 0.8313 | 0.9810 | Pr(UC) > 0.470 | 0.818 | 0.935 |

Figure 6:
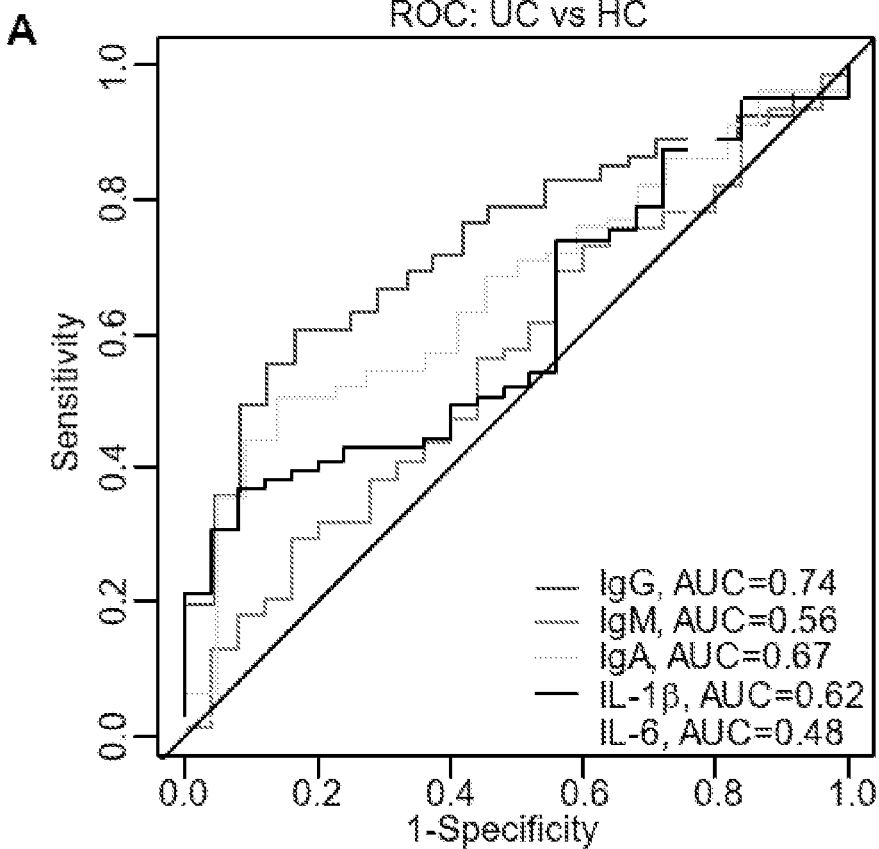
FIG. 6, panels A-F, shows that AUROC curves support diagnostic performance of IgG anti-MAA as biomarker for the detection UC in Nebraska/adult cohort. Panels A-C) ROC analysis for UC vs HC; CD vs HC and UC vs CD. Panels D-F) ROC curve analysis with IL-1β and IL-6 for UC vs HC; CD vs HC and UC vs CD.
Figure 7:
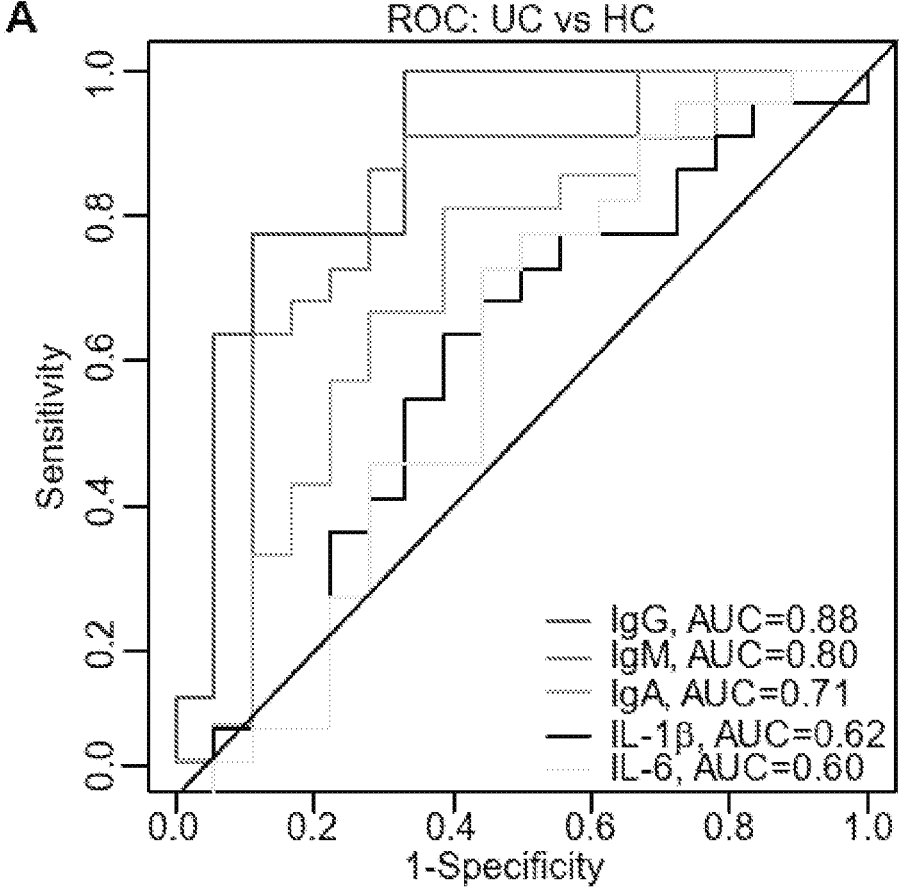
FIG. 7, panels A-F, shows AUROC analysis of IgG anti-MAA immunoglobulins in IBD discriminating that only IgG can differentiate UC from CD in Cincinnati/pediatric cohort. Panels A-C). ROC analysis for UC vs HC; CD vs HC and UC vs CD. Panels D-F) ROC curve analysis with IL-1β and IL-6 for UC vs HC; CD vs HC and UC vs CD.

Discriminating Power of Serum Anti-MAA IgG in Differentiating UC From CD:

We have found a potent association of anti-MAA antibodies in UC that could provide a causal relationship. However, the odds ratio cannot the measure of the anti-MAA IgG diagnostic performance. Therefore, we examined the discriminating potential of immunoglobulin isotypes in the diagnosis of UC from CD. A receiver operator characteristic (ROC) curve analysis was utilized to evaluate the diagnostic power of serum IgG anti-MAA in differentiating UC from CD. As shown in FIG. 6, panels A-C, and Table 7, serum IgG anti-MAA antibody level have significant power to separate UC from CD and HC. Addition of IL-1β and IL-6 further strengthen the discriminatory power of serum IgG anti-MAA (FIG. 6, panels D-F). Area under ROC (AUROC) was 0.8419 (95% CI: 0.751-0.932), with the sensitivity of 0.753, the specificity of 0.857, which was significantly higher than that of IgM and IgA (p=0.0002; FIG. 6, panel F, Table 7). Further, as shown in Table 7, anti-MAA IgG can discriminate UC from CD by >0.799 probability. Moreover, results from IgM and IgA by using logistic regression analysis revealed that the levels of these isotypes were not able to distinguish UC from CD (Table 7). Therefore, these results suggest that serum anti-MAA IgG can discriminate from UC from CD with high sensitivity and specificity at diagnosis.

Figure 5:
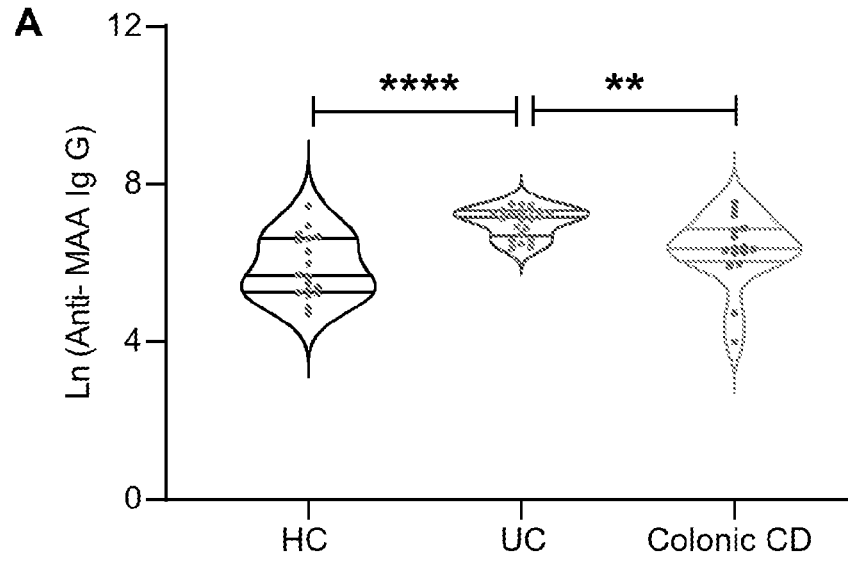
FIG. 5, panels A-C, shows that serum anti-MAA IgG classify UC from colonic CD. Blood ELISA and logistic analysis were done between UC and colonic CD. Panel A) Blood anti-MAA IgG level significantly stratified UC from colonic CD. Panel B) ROC for curve UC vs colonic CD. Panel C) ROC curve analysis with IL-1β and IL-6 for UC vs colonic CD. Values are presented as natural log transformed scale P<0.01 and **P<0.0001.
Figure 9:
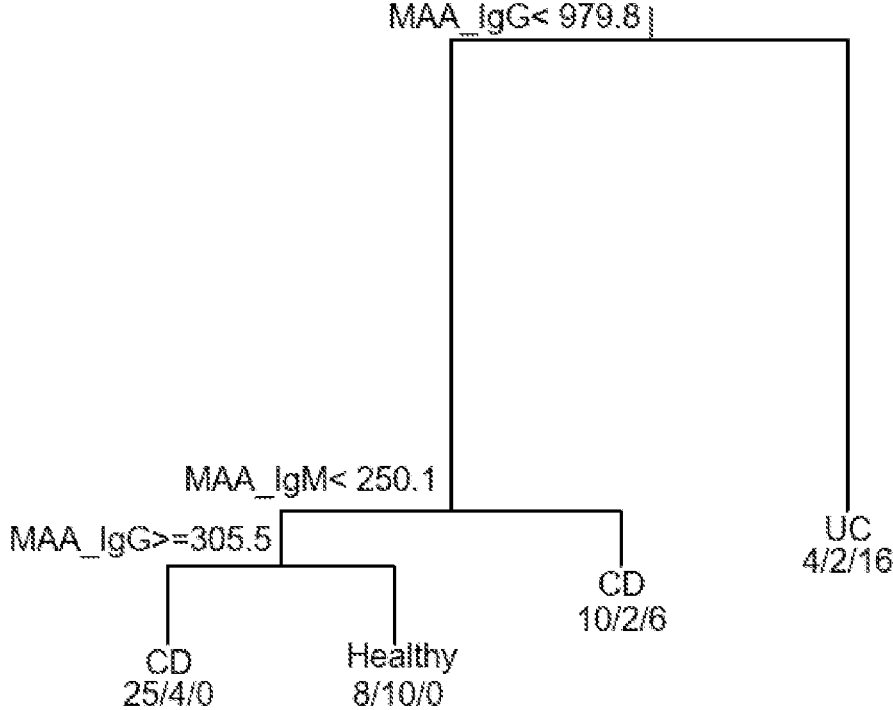
FIG. 9 shows a decision tree that supports the interpretation of anti-MAA IgG biomarker in IBD. The decision tree shows accuracy of anti-MAA IgG to predict UC from CD.

Finally, we determined if anti-MAA Immunoglobulin isotypes can predict disease among UC, CD, and HC. Optimal cutoffs were assigned and ROC curves were generated for the pediatric cohort. Similar results were obtained when logistical regression was performed on the data from the pediatric cohort (UC vs HC and CD vs HC; FIG. 6, panels A-C; Table 8). Interestingly, ROC curve analysis showed that IgG anti-MAA was the strongest predictor between UC and CD with AUROC 0.8801 (95% CI 0.7988-0.9614, p<0.0001), with the sensitivity of 0.955, the specificity of 0.723 (FIG. 6, panel C; Table 8). The AUC for IgG anti-MAA is further increased with the addition of IL-1β and IL-6 (FIG. 6, panels D-F). As shown in FIG. 6, panel F and Table 8, the AUROC was 0.9061 (95% CI: 0.8313-0.9810), with the sensitivity of 0.818, the specificity of 0.935 while the estimated probability was >0.470. Interestingly, IgA anti-MAA was also a significant predictor of UC albeit with poor specificity of 0.400 (P<0.05) (Table-7). IgM anti-MAA value was close to significance (p=0.059) for the diagnosis of UC however specificity was poor (0.487), making it an unlikely candidate as a useful biomarker (Table 8). Since, CD with colon involvement can be difficult to separate from UC, we also analyzed samples from patients with colonic CD to UC. As shown in FIG. 5, panels B-C, AUROC of anti-MAA IgG was significantly discriminatory for UC from the colonic CD. Decision trees were created to predict the diagnosis of UC, CD, or HC (FIG. 9) based on the ROC curves and multivariate analysis. The outcome from the pediatric cohort suggested that at serum anti-MAA IgG level ≥979.8, UC is predictable. In contrast, CD is anticipated if the IgG anti-MAA level is <979.8, with ≥250.1 IgM anti-MAA. If IgM anti-MAA is <250.1 and IgG anti-MAA is 305.5≤ or <979.8 then CD is the most likely diagnosis. Finally, if IgM anti-MAA is <250.1 and IgG anti-MAA is <305.5 then there is no disease present, and one would consider HC as the diagnosis (Supplementary FIG. 9). Overall, the results from these two independent cohorts and IBD biopsies suggest that IgG anti-MAA displayed a better discriminatory performance over IgM and IgA anti-MAA antibodies in differentiating UC from CD. Our data may help to delineate a clinical utility of MAA-adducts and IgG anti-MAA antibodies in the diagnosis of UC, especially when it comes to distinguishing UC from CD localized to colon.

Discussion

In the study, we have demonstrated an increase in the anti-MAA immunoglobulin isotype responses in patients with IBD. Finally, the study results in novel findings that serum IgG anti-MAA levels demonstrate excellent performance characteristics in identifying IBD patients from healthy controls, and further distinguishing UC patients from the CD patients at a high level of specificity and confidence.

Increased oxidative stress and MDA have been reported in several chronic inflammatory diseases, including IBD[17,18]. However, this is the first report suggesting that MDA derived MAA-adducts increase in IBD patients versus healthy controls. These results are in line with those obtained by others who measured elevated MAA-adducts and suggested its importance in chronic diseases, including; rheumatoid arthritis, alcoholic liver disease, lung injury, and cardiovascular disease[3-6]. Interestingly, a significant immune reactivity of the anti-MAA antibody was observed in biopsy samples from UC patients. While studies have shown that MDA concentrations are elevated in both the UC and CD patients compared to normal[19], it may be a possibility that the production of MAA-adducts in UC and CD is independent of oxidative stress and more dependent on the differential antioxidant responses in these two subtypes of IBD[20]. Thus, this process evolves through diverging pathways in CD and UC. The present study unveils that MAA adduct formation could play an important role in IBD pathogenesis and highlights the potential for therapeutic targeting.

The recent recognition is that the MAA adduct is a terminal and stable adduct of MDA that is highly immunogenic and initiates strong innate and acquired responses[2,7]. Studies have further suggested that an increase in anti-MAA antibodies has a major impact on certain inflammatory disease states[2-5,8]. However, the reactivity of one isotype of immunoglobulins over another to the MAA-adduct would indicate a highly specific immune response[2,5,7]. Herein, we begin to fill that gap by reporting that blood IgG anti-MAA is preferentially developed over IgM and IgA in IBD patients. Remarkably, both cohorts, termed as the adult and pediatric cohort, showed a significant increase in anti-MAA IgG isotype over IgM and IgA in IBD patients than healthy control despite the major changes in the age in both patient cohorts. Our findings are consistent with earlier reports that suggest that a rise of IgG serum level in other inflammatory diseases[2-5,7]. Subsequently, circulating levels of anti-MAA immunoglobulin have been shown to correlate with the extent of tissue damage in acute injury and chronic disease states[21]. Specific switching of the immune response to IgG anti-MAA over other isotypes in IBD could be due to the extent and duration of chronic injury, inflammation, and cytokine milieu compared to normal[22]. Also, the literature has shown that IgM is initially produced upon contact with new or "acute" antigens, and then switches to IgG on chronic or repeated exposure to that same antigen[23]. Thus, the reactivity of the IgG isotype to an MAA-adducts would indicate a chronic and highly specific immune response. Additionally, on recurrent tissue injury and inflammation in IBD, MAA-adducts would be released at higher concentrations and alter immune sensitization pathways to initiate pro-inflammatory responses, resulting in the IgG isotype switch over to IgM and IgA.

Unexpectedly, linear regression and ROC analysis, using the adults and pediatric cohort, suggests that IgG anti-MAA is able to discriminate and can predict UC patients from CD with a high sensitivity and specificity. Interestingly, the individuals from these two cohorts belong to two different age groups; one is adult, and the other is younger. Yet, a similar increase in the magnitude of serum IgG levels in both old and younger individuals was observed and indicates that IgG is generated during UC development regardless of age and may serve as a useful biomarker for all UC patients[24,25].

In summary, our study indicates that increased levels of the MAA-adduct and IgG antibodies to this adduct are the direct and useful markers for oxidative stress-mediated tissue injury and immune response in patients with IBD. Surprisingly, this study suggests that high serum levels of IgG anti-MAA combined with immune-staining for MAA-adducts, may facilitate the diagnosis of patients with UC and CD who have a potential crossover of the pathobiology and symptoms at the early stage of life. Also, this study forms the basis for providing a novel outline in understanding and categorizing IBD patients. Further comprehensive studies are needed to understand the underlying mechanisms and diagnostic significance.

REFERENCES

1. Pizzino G, Irrera N, Cucinotta M, et al. Oxidative Stress: Harms and Benefits for Human Health. Oxid Med Cell Longev 2017; 2017:8416763.
2. Tuma D J, Thiele G M, Xu D, et al. Acetaldehyde and malondialdehyde react together to generate distinct protein adducts in the liver during long-term ethanol administration. Hepatology 1996; 23:872-880.
3. Hill G E, Miller J A, Baxter B T, et al. Association of malondialdehyde-acetaldehyde (MAA) adducted proteins with atherosclerotic-induced vascular inflammatory injury. Atherosclerosis 1998; 141:107-116.
4. Sapkota M, Burnham E L, DeVasure J M, et al. Malondialdehyde-Acetaldehyde (MAA) Protein Adducts Are Found Exclusively in the Lungs of Smokers with Alcohol Use Disorders and Are Associated with Systemic Anti-MAA Antibodies. Alcohol Clin Exp Res 2017; 41:2093-2099.
5. Mikuls T R, Duryee M J, Rahman R, et al. Enrichment of malondialdehyde-acetaldehyde antibody in the rheumatoid arthritis joint. Rheumatology (Oxford) 2017; 56:1794-1803.
6. Anderson D R, Duryee M J, Shurmur S W, et al. Unique antibody responses to malondialdehyde-acetaldehyde (MAA)-protein adducts predict coronary artery disease. PLoS One 2014; 9: e107440.
7. Willis M S, Thiele G M, Tuma D J, et al. T cell proliferative responses to malondialdehyde-acetaldehyde haptenated protein are scavenger receptor mediated. Int Immunopharmacol 2003; 3:1381-1399.
8. Willis M S, Klassen L W, Tuma D J, et al. Adduction of soluble proteins with malondialdehyde-acetaldehyde (MAA) induces antibody production and enhances T-cell proliferation. Alcohol Clin Exp Res 2002; 26:94-106.
9. Pedersen J, Coskun M, Soendergaard C, et al. Inflammatory pathways of importance for management of inflammatory bowel disease. World J Gastroenterol 2014; 20:64-77.
10. Piechota-Polanczyk A, Fichna J. Review article: the role of oxidative stress in pathogenesis and treatment of inflammatory bowel diseases. Naunyn Schmiedebergs Arch Pharmacol 2014; 387:605-620.
11. Schumacher M H N, Schwarzer G, Sauerbrei W Prognostic Factor Studies. New York, Basel: Marcel Dekker, 2001.
12. Hothorn T, Hornik K, Zeileis A. Unbiased Recursive Partitioning: A Conditional Inference Framework. Journal of Computational and Graphical Statistics 2006; 15:651-674.
13. Team RDC. Journal of Computational and Graphical Statistics. Vienna, Austria, 2006.
14. Hendrickson B A, Gokhale R, Cho J H. Clinical aspects and pathophysiology of inflammatory bowel disease. Clin Microbiol Rev 2002; 15:79-94.
15. Ahluwalia B, Moraes L, Magnusson M K, et al. Immunopathogenesis of inflammatory bowel disease and mechanisms of biological therapies. Scand J Gastroenterol 2018; 53:379-389.

US 12,571,795 B2

39

40

16. Hedrick T L, Friel C M. Colonic crohn disease. Clin Colon Rectal Surg 2013; 26:84-9.

17. Ahmad R, Tripathi A K, Tripathi P, et al. Malondialdehyde and protein carbonyl as biomarkers for oxidative stress and disease progression in patients with chronic myeloid leukemia. In vivo 2008; 22:525-528.

18. Alzoghaibi M A, Al Mofleh I A, Al-Jebreen A M. Lipid peroxides in patients with inflammatory bowel disease. Saudi J Gastroenterol 2007; 13:187-190.

19. Bouzid D, Gargouri B, Mansour R B, et al. Oxidative stress markers in intestinal mucosa of Tunisian inflammatory bowel disease patients. Saudi J Gastroenterol 2013; 19:131-135.

20. Haberman Y, Karns R, Dexheimer P J, et al. Ulcerative colitis mucosal transcriptomes reveal mitochondriopathy and personalized mechanisms underlying disease severity and treatment response. Nat Commun 2019; 10:38.

21. Rolla R, Vay D, Mottaran E, et al. Detection of circulating antibodies against malondialdehyde-acetaldehyde adducts in patients with alcohol-induced liver disease. Hepatology 2000; 31:878-884.

22. Friedrich M, Pohin M, Powrie F. Cytokine Networks in the Pathophysiology of Inflammatory Bowel Disease. Immunity 2019; 50:992-1006.

23. A. Murphy CJBRH. Chapter 6—Adaptive Immune Responses to Infection: Acaddemic Press, 2017.

24. Cosnes J, Gower-Rousseau C, Seksik P, et al. Epidemiology and natural history of inflammatory bowel diseases. Gastroenterology 2011; 140:1785-1794.

25. Rogers B H, Clark L M, Kirsner J B. The epidemiologic and demographic characteristics of inflammatory bowel disease: an analysis of a computerized file of 1400 patients. J Chronic Dis 1971; 24:743-773.

Supplementary Methods

Estimation of Circulating Serum Anti-MAA Immunoglobulin:

A Enzyme-linked immunosorbent assay (ELISA) was used to estimate the levels of anti-MAA Immunoglobulins in the serum from UC, CD, and healthy controls. Briefly, aqueous human serum albumin (HSA) (Talecris Biotherapeutics, Inc., Research Triangle Park, NC) was modified with MAA (2:1 molar ratio). High-affinity binding ELISA plates were incubated with HSA, HSA-MAA and human IgM, IgG, or IgA isotype standard controls for relative antibody concentration (Sigma Chemical Company, St. Louis, MO) overnight at 4° C. Plates were washed with PBS-T, blocked in 2% casein, and incubated with patient serum at a 1:100 dilution.

Following a 1 hour incubation at 37° C., plates were washed in PBS-T and incubated with the secondary antibodies HRP goat anti-human antibody specific for IgM (Fc5u fragment specific), IgG (Fcγ specific) or IgA (α chain particular) (Jackson Immuno-Research, West Grove, PA). Plates were incubated for an additional hour, washed with PBS-T and developed with TMB substrate, reaction stopped with sulfuric acid, and absorbance was determined at 450 nm using an EpochPlate reader (BioTek, Winooski, VT) and analyzed using Gene 5 Software (BioTek). A human calibrator sample (specific to MAA antigen) was used as a positive control and to keep consistency between plates, and all data were normalized to this sample. The lowest detectable limit for this assay was five relative units of the antibody. Therefore, anything at or below this level was removed from the analysis.

Immunofluorescence Analysis:

Immunofluorescence method of cellular localization was used to detect MAA expression and localization Immunofluorescent staining was performed on slide sections from de-identified endoscopic biopsies from IBD patients by using a rabbit polyclonal antibody specific to MAA directly labeled with a Zenon 405 reporter (Molecular Probes, Eugene, OR). Briefly, antigen retrieval in dewaxed slides was performed using citrate buffer (pH-6.0) and heating to 62° C., followed by blocking in 2% goat serum. The anti-MAA antibody and control isotype at a concentration of 1:100 was used for overnight incubation. Slides were then washed with PBS three times and mounted with coverslips. Stained tissues were analyzed using a Zeiss 710 confocal microscope accompanied by ZEN black Software (Zeiss) and quantification of images with Image J using the FIJI plugin (National Institutes of Health).

Cytokines Estimation:

Multiplex analysis was performed on patient serum using a U-PLEX™ immunoassays (Meso Scale Discovery, Rockville, MD) for IL-1β and IL-6. The assays were performed according to the manufacturer's protocol and analyzed on the MESO QuickPlex SQ 120 imager (Meso Scale Discovery).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating a subject, the method comprising:
detecting a level of immunoglobulin G (IgG) antibodies that bind a malondialdehyde-acetaldehyde (MAA) adduct in a biological sample of a human subject having at least one symptom of ulcerative colitis or Crohn's disease, wherein the biological sample is selected from the group consisting of whole blood, blood plasma, and blood serum;
comparing the level of the IgG antibodies that bind the MAA adduct to an average level in another human subject with the Crohn's disease;
determining that the level of the IgG antibodies that bind the MAA adduct is higher than the average level in the other human subject with the Crohn's disease;
identifying the human subject as having the ulcerative colitis; and
administering a pharmaceutical to the human subject to treat the ulcerative colitis.

2. The method of claim 1, wherein the level of the IgG antibodies that bind the MAA adduct is at least 1.2 times greater than the average level in the other human subject with the Crohn's disease.

3. The method of claim 1, further comprising: performing a surgical procedure on the human subject to remove a damaged portion of intestines of the human subject to treat the ulcerative colitis.

4. The method of claim 1, further comprising:
detecting a level of at least one inflammatory biomarker in the biological sample;
comparing the level of the at least one inflammatory biomarker to an average level of the at least one inflammatory biomarker in the other human subject with the Crohn's disease; and determining that the level of the at least one inflammatory biomarker is higher than the average level in the other human subject with the Crohn's disease.

5. The method of claim 4, wherein each inflammatory biomarker of the at least one inflammatory biomarker is selected from the group consisting of interleukin-6 (IL-6) and interleukin-1 beta (IL-1β).

6. The method of claim 4, wherein the at least one inflammatory biomarker is interleukin-6 (IL-6) and interleukin-1 beta (IL-1β).

7. The method of claim 1, wherein the level of the IgG antibodies that bind the MAA adduct is at least 1.5 times greater than the average level in the other human subject with the Crohn's disease.

8. The method of claim 1, wherein the level of the IgG antibodies that bind the MAA adduct is at least 1.8 times greater than the average level in the other human subject with the Crohn's disease.

9. The method of claim 1, wherein the level of the IgG antibodies that bind the MAA adduct is at least 2 times greater than the average level in the other human subject with the Crohn's disease.

10. The method of claim 1, wherein the level of the IgG antibodies that bind the MAA adduct has a p value of $p < 0.05$.

11. The method of claim 1, wherein the level of the IgG antibodies that bind the MAA adduct has a p value of $p < 0.01$.

12. The method of claim 3, wherein the pharmaceutical is selected from the group consisting of an anti-inflammatory agent, an immunosuppressant agent, a monoclonal antibody, an antibiotic, and an antidiarrheal agent.

13. The method of claim 12, wherein the anti-inflammatory agent is selected from the group consisting of sulfasalazine, mesalamine, and olsalazine.

14. The method of claim 12, wherein the immunosuppressant agent is selected from the group consisting of azathioprine and tacrolimus.

15. The method of claim 12, wherein the monoclonal antibody is selected from the group consisting of infliximab, adalimumab, certolizumab, and vendolizumab.

16. The method of claim 12, wherein the antibiotic is selected from the group consisting of ampicillin, cefotaxime, ciprofloxacin, and tetracycline.

17. The method of claim 12, wherein the antidiarrheal agent is loperamide.

* * * * *